(12) United States Patent
Boisseau et al.

(10) Patent No.: US 9,731,149 B2
(45) Date of Patent: Aug. 15, 2017

(54) METHOD AND APPARATUS FOR MEASURING, VERIFYING, AND DISPLAYING PROGRESS OF DOSE DELIVERY IN SCANNED BEAM PARTICLE THERAPY

(71) Applicant: Pyramid Technical Consultants, Inc., Lexington, MA (US)

(72) Inventors: Raymond Paul Boisseau, Waltham, MA (US); William P. Nett, Waltham, MA (US); John S. Gordon, Arlington, MA (US); Sashidar Kollipara, Newton, MA (US); Yuriy Kozlov, Belmont, MA (US)

(73) Assignee: Pyramid Technical Consultants Inc., Lexington, MA (US)

( * ) Notice: Subject to any disclaimer, the term of this patent is extended or adjusted under 35 U.S.C. 154(b) by 356 days.

(21) Appl. No.: 14/493,098

(22) Filed: Sep. 22, 2014

(65) Prior Publication Data

US 2015/0087885 A1  Mar. 26, 2015

Related U.S. Application Data

(60) Provisional application No. 61/880,954, filed on Sep. 22, 2013.

(51) Int. Cl.
*A61N 5/10* (2006.01)
*G01N 23/22* (2006.01)
*H01J 37/244* (2006.01)

(52) U.S. Cl.
CPC ......... *A61N 5/1067* (2013.01); *A61N 5/1043* (2013.01); *A61N 5/1071* (2013.01); *A61N 2005/1087* (2013.01)

(58) Field of Classification Search
CPC .. A61N 5/1071; A61N 5/1031; A61N 5/1043; A61N 5/1048; A61N 5/00;
(Continued)

(56) References Cited

U.S. PATENT DOCUMENTS 7,636,419 B1 * 12/2009 Nelson ................. A61N 5/1048
250/363.01
7,945,022 B2 * 5/2011 Nelms .................. A61N 5/1071
378/65

(Continued)

OTHER PUBLICATIONS

Jiang et al., "On dose distribution comparison", Phys. Med. Biol., 2006, p. 759-776, vol. 51,IOP Publishing Ltd., UK.
(Continued)

*Primary Examiner* — David A Vanore
(74) *Attorney, Agent, or Firm* — Intrinsic Law Corp.

(57) ABSTRACT

The present disclosure is directed to systems and methods for real-time control of a charged particle pencil beam system during therapeutic treatment of a patient. In an aspect, the present disclosure is directed to measuring an actual shape, an actual intensity distribution, and an actual location at isocenter of the charged particle pencil beam. The actual data is compared to model treatment data in real time to determine if a statistically significant variance occurs in which case the charged particle pencil beam can be stopped mid-treatment for correction and/or analysis.

9 Claims, 20 Drawing Sheets

(58) Field of Classification Search
CPC ........ A61N 5/10; A61N 5/103; A61N 5/1038;
A61N 5/1039; A61N 5/1047; A61N
5/1065; A61N 5/1067; A61N 5/1075;
A61N 5/1077; G01N 23/22; G01N
23/223; G01N 23/2251; G01N 23/046;
H01J 37/09; H01J 37/10; H01J 37/20;
H01J 37/222; H01J 37/244; H01J 37/265;
H01J 37/28; H01J 37/29
USPC ......... 378/65, 17, 20, 4, 62; 250/492.3, 306,
250/309, 310, 311, 336.1, 363.01, 393,
250/491.1; 600/1
See application file for complete search history.

(56) References Cited

U.S. PATENT DOCUMENTS

| | | | |
|---|---|---|---|
| 8,497,476 B2* | 7/2013 | Hatakeyama | G01N 23/2251 250/306 |
| 8,541,762 B2* | 9/2013 | Claereboudt | A61N 5/1043 250/492.3 |
| 8,693,618 B2* | 4/2014 | Tischenko | A61B 6/032 378/17 |
| 8,716,663 B2* | 5/2014 | Brusasco | A61N 5/1048 250/336.1 |
| 9,089,696 B2* | 7/2015 | Verhaegen | A61N 5/1047 |
| 9,220,920 B2* | 12/2015 | Schulte | A61N 5/1039 |
| 9,289,627 B2* | 3/2016 | Otto | A61N 5/1031 |
| 2011/0248188 A1 | 10/2011 | Brusasco et al. | |
| 2014/0014848 A1* | 1/2014 | Hatakeyama | G01N 23/2251 250/393 |
| 2015/0087885 A1* | 3/2015 | Boisseau | A61N 5/1043 600/1 |
| 2016/0199667 A1* | 7/2016 | Flynn | A61N 5/1043 600/1 |

OTHER PUBLICATIONS

Li et al., "Use of treatment log files in spot scanning proton therapy as part of patient-specific quality assurance", Med. Phys., Feb. 2013, vol. 40—issue 2, American Association of Physicists in Medicine.

* cited by examiner

METHOD AND APPARATUS FOR MEASURING, VERIFYING, AND DISPLAYING PROGRESS OF DOSE DELIVERY IN SCANNED BEAM PARTICLE THERAPY

TECHNICAL FIELD

This invention relates to charged particle pencil beam therapy and, more particularly, to systems and methods for monitoring dosage levels and progress of charged particle pencil beam therapy.

RELATED APPLICATIONS

This application is related and claims priority to U.S. Provisional Application No. 61/880,954 entitled, "Method and Apparatus for Measuring, Verifying, and Displaying Progress of Dose Delivery in Scanned Beam Particle Therapy" filed on Sep. 22, 2013, which is hereby incorporated by reference.

BACKGROUND

Particle beam therapy is a therapeutic method that has been developed primarily for the treatment of certain cancers, in preference to conventional x-ray radiation therapy. The technique uses an energetic beam of ions to target the tumor with a higher degree of precision, making it the treatment of choice for some cancers. The specific property of the ion beam is its ability to deliver dose deep into the target with minimal dose to the tissues in front or in back of the target position.

The effectiveness of the method is dependent on the ability of the delivery system to accurately deliver a specified, three-dimensional distribution of dose. This task can be divided into two parts. The first part is to control the depth of the beam into the target. This is done through control of the beam energy. The second part is the need to control the beam in the lateral dimension, perpendicular to the beam direction.

In the method that has dominated the field, known as Double Scattering, the beam is formed into a wide beam with dimensions larger than the target tumor. Collimators near the patient are used to define the lateral shape of the beam. Typically, the beam energy is periodically modulated in a number of discrete steps and over a time scale of 100 milliseconds though an energy degrader mechanism. In this way, the entire volume of the tumor is irradiated "at once". When properly executed, a double-scattering treatment will proceed until a predetermined total dose has been delivered In the newer method known as Pencil-Beam Scanning, a much narrower beam is used to "draw" the three-dimensional dose distribution. Lateral positioning of the beam is done through the use of a magnetic deflection system. Typically, the treatment is divided into discrete energy steps, in which a two-dimensional distribution is delivered for each energy in turn, building up the full three-dimensional distribution as the treatment progresses.

PBS is becoming the mode of preference due to the elimination of the need for physical collimators and other hardware, and its ability to create arbitrary three-dimensional distributions, a capability that does not exist for double scattering.

PBS is typically operated in "spot-scanning" mode in which the beam is directed to the target lateral position with the beam disabled. The beam is then enabled and a predetermined target dose is delivered. The beam is then disabled, which results in an actual dose that may have a deviation from the specified target. An appropriate characterization of, and reaction to such errors is a key aspect of this patent.

Any treatment method requires a control system to execute the desired treatment. An important aspect of such a control system is the ability to monitor the progress of the treatment to ensure accuracy of the final dose distribution, and to react to process deviations that could result in a potentially dangerous dose error.

The monitoring function requires the ability to quantify the beam delivered to the patient during treatment. In the case of double scattering, this takes the form of an inline detector to verify the uniformity of the scattered beam at the collimator position, in addition to a total dose detector.

In the case of pencil-beam scanning, the similar monitoring hardware is typically used, with minimal changes in the monitoring software. As a result, the specific process parameters that arise through the use of PBS are not properly accounted for. As a result, existing PBS systems exhibit a number of problematic characteristics, chief among them a high rate of process interruptions.

Elimination of the existing problems with the PBS monitoring process requires the design of innovative new hardware, and the application of calculation-intensive real-time analysis algorithms. The general approach is to measure both the beam trajectory and the beam shape at each moment in the scanning process, and to incorporate this information into an analysis that properly predicts the dose distribution actually delivered to the patient as the process is occurring.

The primary measurement needed in the monitoring and control of a therapeutic ion beam is that of the beam position and intensity profile at various points in space. One generally accepted method for measuring charged particle (e.g., protons or other ions) beam current is through the use of a transmission ion chamber. In its simplest implementation, this detector consists of two planar electrodes arranged in a parallel configuration spanning a gas-filled layer. A bias voltage is applied between the two electrodes to establish an electric field in the air gap. Current or charge-integrating electronics is attached to one of the electrodes. An example of such a transmission ion chamber detector is illustrated in FIG. 1. Because scanned-beam applications span a large area at the patient position, any ion chambers placed after the scanning magnets must generally be large in area.

As a beam of ionizing radiation (such as charged particles, including protons) passes through the detector in a direction nominally perpendicular to the electrode plane, some fraction of the incident beam energy is lost to the fill gas. The energy lost is a function of incident radiation type, radiation energy, the thickness of the gas gap, and the density of the gas. Given these parameters, the energy loss can be accurately calculated.

One mechanism for the energy loss in the gas is the through ionization, the creation of electron-ion pairs. It has been determined experimentally that there is a fixed relationship between the energy loss and the number of ion-pairs created. This is typically referred to as "W" and has a value of approximately 32 eV/Ion pair. To good accuracy, the rate of creation of electron-ion pairs is proportional to the intensity of the incident irradiation, and the constant of proportionality can be theoretically determined. It is this property, combined with the ease of calculation of energy loss, that has led to the use of the ion chamber in applications requiring accurate, quantitative, and easily calibrated measurement of radiation intensity.

In isolation, these electron-ion pairs would ordinarily recombine in a short time, typically in less than 1 msec. However, the imposed electric field causes the charges to separate and move towards the electrodes, with the electrons moving toward the positive potential, and the positive ions moving toward the negative electrode. An electric field of about 1000V/cm is typically adequate to collect close to 100% of the generated charge, with a small percentage being lost to recombination.

The ion chamber has a gain, a fixed ratio relating the intensity of the incident radiation to the collection ion current. The gain is dependent on the gas density, but has very little dependence on the bias voltage (as long as it is high enough) or the gas species. The gain is energy dependent, but is fixed for any specific beam energy.

There are several variants from the planar detector described above. In general, the planar electrode can be divided into an arbitrary arrangement of smaller electrodes. Each of these new component electrodes will collect charge from the 3-dimensional gas volume defined by the electrode shape projected along the electric field lines. The total collected charge is unchanged from the original configuration. Such subdivisions of the electrode allow the determination of the spatial distribution of the incident radiation beam.

One useful configuration is a strip detector, which is illustrated in FIG. 2. Here, the strip detector 200 includes an electrode plane 210 divided into long, narrow strips 215. The geometry of the strip detector is such that each strip 215 collects charge from a particular lateral position of the beam, but independent of the position in a perpendicular axis 220. This provides the distribution of beam intensity projected onto the perpendicular axis 220. Such detectors can be used in orthogonal pairs, in which case the projection of the beam intensity is determined for two orthogonal axes. This measurement determines the centroid position of the beam in the X, Y plane, since this calculation is dependent only on the orthogonal projection data, and does not require the full 2-dimensional distribution of the beam intensity.

The construction and readout of the strip ion chamber 200 is simplified by the fact that the electrode signal can be extracted at the ends 240 of the electrode strips 215, where an attachment mechanism 250 is outside of an active area 260 of the detector 200. The relatively small number of sensing electrode strips 215 allows the sensing electronics to remain simple.

In cases in which the full two-dimensional distribution of the charged particle beam cross-section is needed, the electrode plane can be divided into an array of square or rectangular sub-electrodes or "pixels." Here, the problem of extracting the signals is more complex. It is necessary to bring the signals from the individual pixels to a point of external connection through conductive traces.

One solution is to create traces on the surface that contains the pixels themselves. A shortcoming of this approach is that these conductive traces will themselves become collecting electrodes, distorting the resulting data. However, this approach simplifies the construction, since the traces can be created as part of the processing step that is used to create the pixels. This approach adds no additional material to the detector, and so can provide the thinnest construction.

An alternative solution is to dispose the conductive traces on the back side of the sensing electrode, where there is no electric field, and therefore no charge collection on the traces. This requires the use of through-plane electrical "vias" to connect the rear traces to the individual pixels. FIG. 3 illustrates a front side 310 and a back side 320 of a pixelated ion chamber detector 300. This method is less attractive, requiring more complex manufacturing processes.

For applications requiring small beam spots at the patient position, an important specification of the ion chamber is its effect on the beam spot size through the mechanism of scattering. Scattering increases the beam's emittance, which is a measure of the optical quality of the beam, and relates directly to the ability to focus the beam to a small spot. The location of the scattering object is also important as the further the beam is from the target when the scattering occurs, in general the more pronounced its effect is at the target location.

For the purpose of measuring the beam cross-sectional intensity distribution, it is preferable to measure the beam shape close to the patient, since this is the measurement most representative of the beam striking the patient. This is impractical because of the resulting large number of pixels required to span the large scan area (typically 30×40 cm) with adequate resolution. It is advantageous to monitor the beam as close as possible, but preceding the scan magnet because the beam is small and stationary, allowing the use of a small detector, a tractable number of pixels (128-1024), and simple electronics. However, this location is far enough from isocenter that scattering is a severe problem, and sufficiently thin ion chambers have not been available from this application. The initial development of particle therapy used mainly passive lateral scattering followed by collimation to conform the beam of particles to the dimensions of the target (e.g., a tumor). In this respect, it is similar to X-ray radiotherapy, in which a broad fan of X-rays is collimated to conform to the target dimensions.

Since depth of treatment is a function of particle energy, any treatment method must modulate the beam energy. In the commonly used "double scattering" technique, the beam energy is modulated at high speed, and a broad beam is delivered to the patient position, spanning the entire tumor volume at the same time. In the newer, scanned beam method, the area of the tumor is drawn with a narrow beam typically at a single energy, and this process is repeated for each of a set of energies, thus building up the required depth profile.

In general, scattered particle therapy treatment systems rely on arrangements calculated and made before the treatment starts to control the lateral distribution of dose, for example the use of custom-machined collimating apertures. Thus, while the treatment is in progress, the supervising therapist need only monitor the accumulation of overall dose (e.g., by monitoring a dose counter) to ensure that it reaches the specified total, at an acceptable rate, without significant under- or overdose. In this respect, the methods of dose delivery monitoring and therapist oversight of the process are the same as those used for X-ray radiotherapy, to the extent that the applicable standards are identical or closely related.

A more recent means of delivering conformal dose with particle beams is the use of active beam deflection, or scanning, often called pencil beam scanning (PBS). A small beam spot with adjustable intensity is moved over the target area by deflecting a mono-energetic beam using fast electromagnets, according to a pre-calculated trajectory. The process is repeated for each of a set of energies. This method provides a finer control of where dose is delivered, and allows essentially arbitrary lateral distribution profiles, unconstrained by the mechanical limitations imposed by collimating apertures. The lack of such apertures also reduces the generation of unwanted neutrons close to the patient, which produce untargeted radiation dose. Pencil beam scanning is an essential component of most new particle beam therapy installations, and seems destined to become the primary dose delivery means.

PBS introduces a new complication to the monitoring, interlocking and oversight of the dose delivery. Since the PBS beam covers only a small fraction of the tumor at any given time, in order to irradiate the width of the tumor, the PBS beam must be scanned laterally across a plane that is perpendicular to the PBS beam.

Although PBS beam scanning introduces new error sources (e.g., the position of the PBS beam spot on the x-y treatment plane, present system control has not advanced significantly to deal with this new delivery mode. PBS systems still rely on the total dose as an important parameter allowing direct monitoring by the operator. In the commonly used "spot-scanning" mode of PBS, the dose is delivered to discrete locations in sequence. At each such spot, the dose is monitored, with the goal of delivering a particular dose. The error in the delivered dose is monitored, and if it exceeds a preset value, an error condition is generated, resulting in a pause or stop to the process, as well as operator intervention. Because this method looks at one spot at a time, it is not able to consider spatially overlapping, compensating errors. No method now in use monitors the overall delivered distribution for excessive deviation during treatment.

A weakness in existing PBS delivery systems is that the actual dose distribution, such as across the x-y treatment plane for a given energy level, is not determined during treatment. As a result, it is necessary to apply very stringent limits on delivered dose on individual spots. The single-spot monitoring method introduces an excessive number of error conditions. The tendency for overlapping errors to average out is not considered. Such consideration requires the sort of 2d analysis that is the basis of the technique.

A common technique for PBS monitoring is to execute the full treatment plan without the patient present, applying the dose to a volume of water to simulate a therapeutic scan of a patient's tumor, and then comparing the resulting dose to the target distribution. While such a technique can be useful to verify the overall correctness of the treatment plan, it does nothing to account for real-time variations during therapeutic treatment of a patient.

Accordingly, there is a need for PBS systems that do not suffer from some or all of the above problems.

SUMMARY

Aspects of the present disclosure is direct to a system for real-time dosage monitoring during therapeutic treatment of a patient, the system comprising a pencil beam generator to generate a charged particle pencil beam that travels in a direction parallel to a reference axis, the charged particle beam having an intensity distribution and a shape; a first detector disposed in a first plane orthogonal to the reference axis and configured to dynamically generate a first output representative of the shape and the intensity distribution of the charged particle pencil beam, the first detector comprising detector elements that define pixels; a magnetic field generator configured to deflect the charged particle pencil beam, at an angle relative to the reference axis, to a model target location in a patient, wherein the first planar beam detector is disposed between the pencil beam generator and the magnetic field generator; a second detector disposed in a second plane orthogonal to the reference axis, the second detector configured to generate a second output representative of second coordinates of the charged particle pencil beam in the second plane, wherein the magnetic field generator is disposed between the first detector and the second detector; a third detector disposed in a third plane orthogonal to the reference axis, the third detector configured to generate a third output representative of third coordinates of the charged particle pencil beam in a third plane, wherein the second detector is disposed between the magnetic field generator and the third detector; and a controller comprising a processor, the controller configured to receive as inputs the first output, the second output, and the third output and to transmit an intensity control signal to the pencil beam generator and a target location control signal to the magnetic field generator.

Additional aspects of the present disclosure are directed to a method for real-time control of a charged particle pencil beam system during therapeutic treatment of a patient, the method comprising receiving an image of the charged particle pencil beam during treatment of a target spot; measuring an actual shape and an actual intensity distribution of the charged particle pencil beam; determining an actual position of the charged particle pencil beam at an isocenter plane, the actual position corresponding to a location in a pixel of acquired data; comparing actual data for the target spot with target data for the target spot to form comparison data; and automatically stopping the therapeutic treatment if the comparison data is greater than a tolerance.

Additional aspects of the present disclosure are directed to a method for real-time control of a charged particle pencil beam system during therapeutic treatment of a patient, the method comprising receiving a treatment map for therapeutic treatment of a patient using a charged particle pencil beam system, the treatment map comprising an array of target spots; generating an acquired matrix from the treatment map, the acquired matrix comprising pixels having target data corresponding to the array of spots, the target data comprising a target position, a target shape, and a target intensity distribution; removing target data from first pixels corresponding to a first spot from the treatment map; therapeutically treating a spot in a patient with a charged particle pencil beam; measuring an acquired image from a pixelated detector disposed between a charged particle pencil beam source and a magnetic field generator, the acquired image including an actual shape and an actual intensity distribution of the charged particle pencil beam; determining an actual position of the charged particle pencil beam at an isocenter plane; defining an active region of pixels that receive at least some intensity of the charged particle pencil beam; updating the first pixels with acquired data for the active region, the acquired data including the actual position, the actual shape, and the actual intensity distribution of the charged particle beam; comparing the acquired data with target data for each pixel in the active region to generate comparison data; and automatically stopping the therapeutic treatment if the comparison data is greater than a tolerance.

IN THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments and are not therefore to be considered limiting of its scope.

DETAILED DESCRIPTION

For thin scattering layers, the amount of scattering is proportional to the areal density of the scattering material, expressed in grams/cm$^2$. An ion chamber that has minimal effect of the beam spot must therefore have minimal areal density. This can be achieved with low-density material, thin layers (i.e., low total thickness), or a combination of both.

Figure 5:
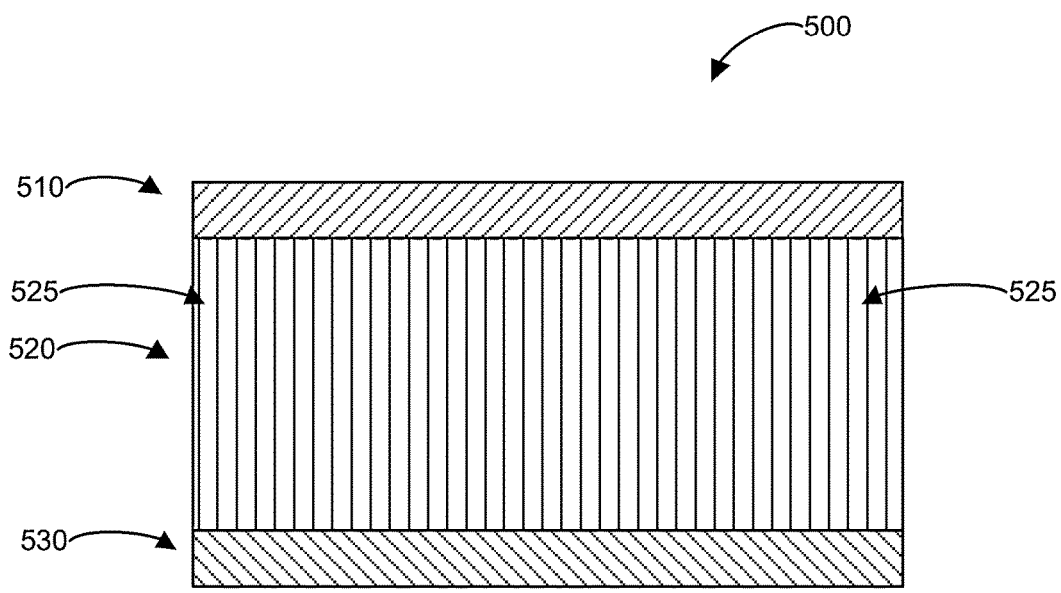
FIG. 5 is a cross-sectional view of an embodiment of an electrode material.

In order to produce a device, such as a pixelated ionization chamber detector, which can be suitable for use upstream in a charged particle pencil beam therapy system, the electrodes for such a device can be manufactured from a metalized non-conducting film. In this application, the supporting film can be nonconductive (e.g., less than about $1 \times 10^{10}$ Ohms/square), can have an areal density of less than about $2 \times 10^{-3}$ gm/cm$^2$ and can be highly radiation resistant. In general, the supporting film can have mechanical properties sufficient to support enough tension to resist gravitational deflection at the scale of microns over a span of several centimeters. In some embodiments, the supporting film is or comprises polyimide. FIG. 5 illustrates a cross-sectional view of an embodiment of the electrode material 500 prior to manufacturing. The electrode material 500 includes a polymer layer 510, a first metal layer 520, and a second metal layer 530. The polymer layer 510 is between the first and second metal layers 510 and 530, respectively. The metal layers 510 and 530 can be about 800, 900, 1000, or 1100 Angstroms thick and can be comprised of aluminum, gold, or other suitable metal known to those skilled in the art. The metal layers 510 and 530 are thin, and therefore have negligible effect of beam scatter. The metal layers 510 and 530 are also highly electrical conductive, which provides a low-resistance path for signal traces.

The polymer layer 520 can be between about 10 and 30 microns thick, including between about 15 and about 25 microns thick, about 12.5 microns thick, or about 20 microns thick. Such a thickness is low enough to create less than or equal to about 1 mm of beam scatter at a distance of about 3 meters for proton beams of clinical interest (e.g., proton beams having an energy of less than 100 MeV). The polymer layer 510 can be a low atomic weight polymer and can have a low areal thickness, as discussed above. In general, the polymer layer 520 can be strong enough to be self-supporting over a span of several centimeters, can be resistant to creep, can have a low coefficient of thermal expansion, and can be radiation resistant for doses in the range of $2 \times 10^6$ Gy. For reference, a typical course of clinical treatment results in a dose of about 60 Gy. Assuming 10 treatments per day, and 300 days of usage per year, a device will accumulate $1.8 \times 10^6$ Gy in 10 years, which can be an acceptable lifetime in the industry. In some embodiments, the polymer layer is polyimide, such as KAPTON® polyimide film available from E. I. du Pont de Nemours and Company. For example, polyimide film has relatively stable mechanical properties up to $1 \times 10^7$ Gy, as indicated in the Table 1. The polymer layer 520 includes vias 525 that extend from the first metal layer 510 to the second metal layer 530.

TABLE 1

| Property | Control 1 mil film | $1 \times 10^4$ Gy | $10^5$ Gy | $10^6$ Gy | $10^7$ Gy |
| --- | --- | --- | --- | --- | --- |
| Tensile Strength Mpa psi × 10$^3$ | 207 30 | 207 30 | 214 31 | 214 31 | 152 22 |
| Elongation (%) | 80 | 78 | 78 | 79 | 42 |
| Tensile Modulus Mpa Psi × 10$^3$ | 3172 460 | 3275 475 | 3378 490 | 3275 475 | 2903 421 |
| Vol. Resistivity ohm-cm × 10$^{13}$ @ 200° C. | 4.8 | 6.6 | 5.2 | 1.7 | 1.6 |
| Diel. Constant 1 kHz @ 23° C. | 3.46 | 3.54 | 3.63 | 3.71 | 3.50 |
| Dis. Factor 1 kHz @ 23° C. | .0020 | .0023 | .0024 | .0037 | .0029 |
| Diel. Strength kV/mm | 256 | 223 | 218 | 221 | 254 |

Figure 6:
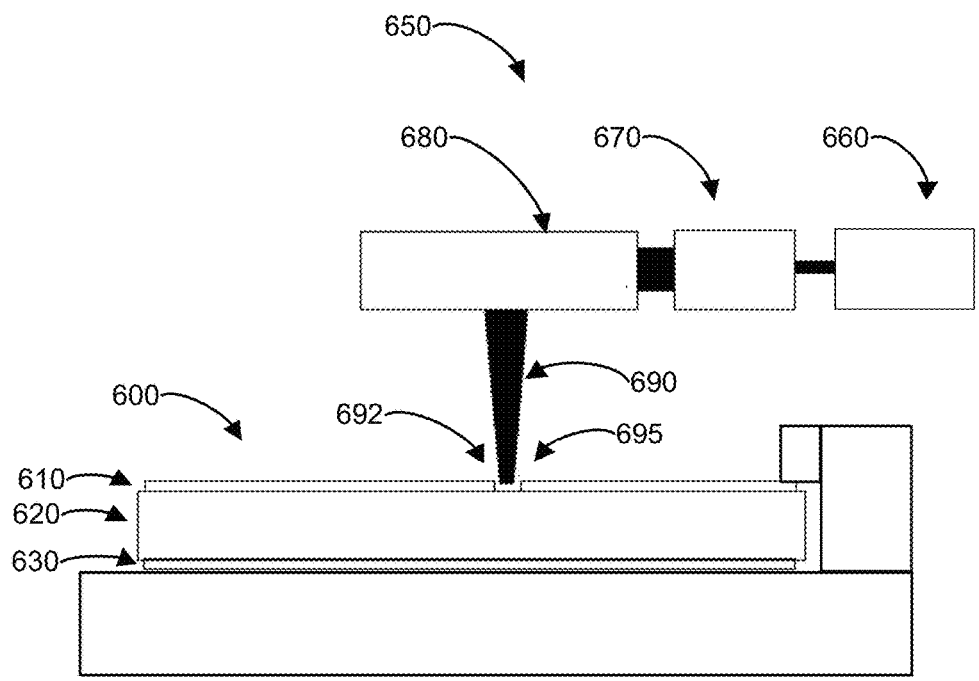
FIG. 6 is an exemplary apparatus for manufacturing a pixelated ionization chamber detector according to an embodiment.

FIG. 6 illustrates an exemplary apparatus for manufacturing a pixelated ionization chamber detector, as discussed above. As illustrated in FIG. 6, the apparatus 650 includes a laser generator 660, a beam expander 670, and a scanning galvanometer and lens 680. The apparatus 650 is configured to direct a laser beam 690 at an electrode material 600, which includes metal layers 610 and 630 and polymer layer 620. The laser generator 660 can generate a fast-pulsed laser 690 (e.g., a pulse length less than or equal to 10 nanoseconds at an energy of at least 5 microJoules per pulse) to ablate and/or explosively vaporize the metal layers 610 and/or 630. The energy of the laser 690 can be high enough to explosively vaporize the metal layer 610 to occur over time scales short compared to thermal relaxation time scales of the metal layer 610. The laser 690 can ablate a portion 695 of the metal layer 610 to form a pixelated electrode structure. The pixelated electrode structure can have dimensions of about 2.0-5.0 mm in the x and/or y directions with a resolution of about 0.5 mm, 0.75 mm, or 1.0 mm per pixel. In addition, the laser 690 can ablate the metal layer 610 to form connecting traces that route the electrical charge from the pixels to a peripheral connection point. In general, the connecting traces should be as narrow as practical to minimize charge pickup. In some embodiments, the laser 690 ablates the metal layer 630 to form connecting traces to a peripheral connection (i.e., the connecting traces and pixels can be on the same metal layer or can be on metal layers on opposing sides of the polymer layer 620).

The laser 690 can have one or more properties. For example, the laser 690 can couple effectively to the metal layers 610, 630. If the metal layers 610, 630 are formed out of aluminum, which is highly reflective, the laser 690 can be in the ultraviolet and/or infrared spectral regions to couple to the metal layers 610, 630. In addition, the laser 690 can be focused to a size of 25 microns or less, such as 20 microns, 15 microns, 10 microns, or 5 microns, to allow the creation of fine structures in the metal layers 610 and/or 630. Shorter wavelengths, such as wavelengths in the ultraviolet spectrum, can have a smaller diffraction-limited spot size for a given optical configuration. Further, the laser 690 is generally not transparent to the polymer substrate 620. In other words, the polymer substrate 620 absorbs at least some of the laser 690 and prevents the laser 690 from ablating the metal layer 630 on the opposing side of the polymer substrate layer 620.

In some embodiments, the first metal layer 610 is ablated to form pixels (as described above), and the second metal layer 630 is ablated to form back-side traces to electrically connect the pixels to external electronics (e.g., a multi-output reader). In some embodiments, the first metal layer 610 is ablated to form pixels (as described above), and the second metal layer 630 is not ablated. In this case, the second metal layer can ground the apparatus 650, for example to prevent free charge from accumulating on the dielectric.

The laser 690 can have a wavelength less than about 400 nm. Such a wavelength can be useful for fabricating the apparatus 650 when polymer substrate layer 620 includes polyimide because polyimide absorbs at least some energy from the laser 690 in that spectrum. It is noted that polyimide becomes transparent at wavelengths longer than about 400 nm, which is less advantageous because the laser 690 can ablate the opposing metal layer (e.g., second metal layer 630) during processing of the other metal layer (e.g., first metal layer 610). In some embodiments, the laser generator 660 is a Q-switched wavelength tripled Ytterbium-doped laser operating at 355 nm. Such a laser generator 660 generates a laser 690 having the properties described above. It is noted that shorter wavelength lasers (e.g., less than 355 nm) can be used, but tend to be more expensive and have lower average power, which can result in increased processing time. The laser 690 is combined with beam expander 670 and a lens (scanning galvanometer and lens 680) to generate a beam spot 692, which can have a diameter of between about 10 microns and about 20 microns, including about 15 microns.

Figure 7:
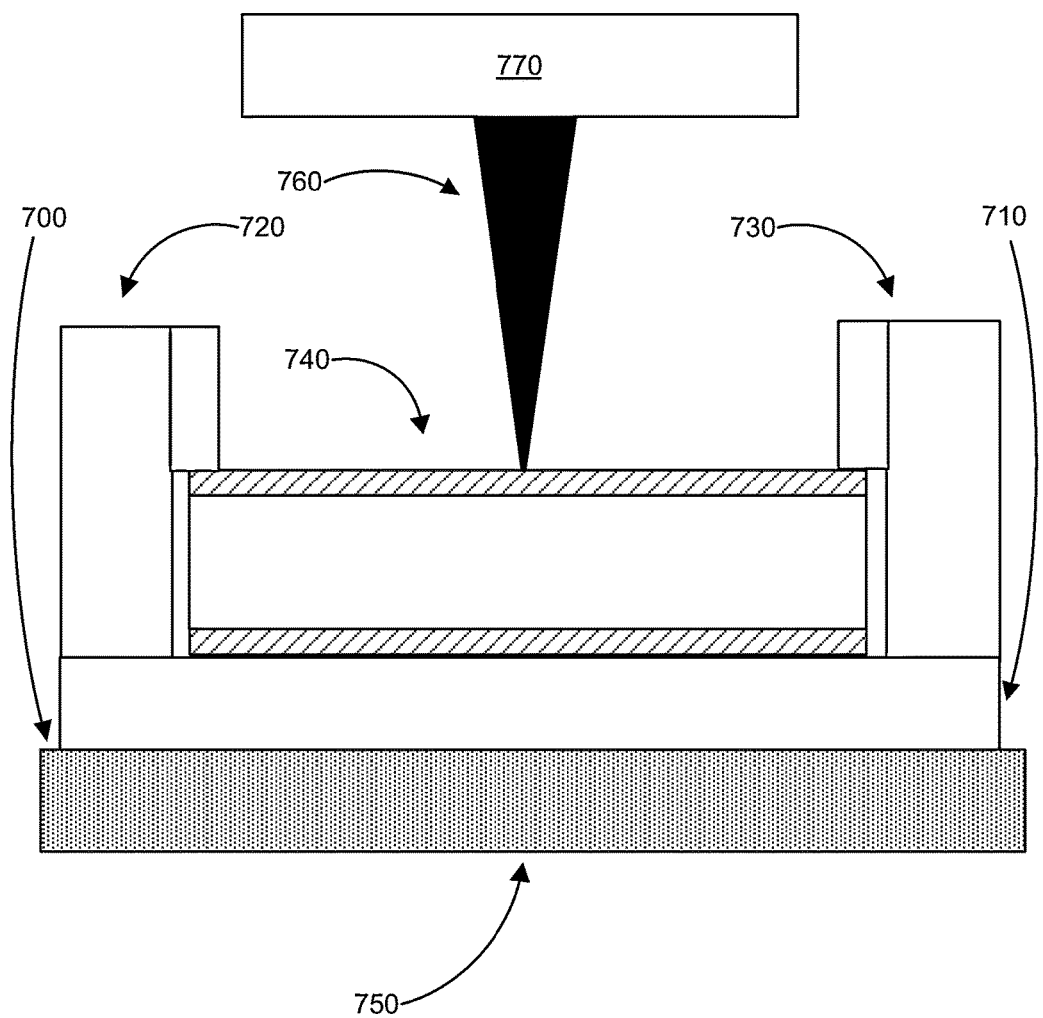
FIG. 7 is a cross-sectional view of a mounting structure and manufacturing stage according to an embodiment.

FIG. 7 illustrates a cross-sectional view of a mounting structure and manufacturing stage according to an embodiment. The mounting structure 700 includes a body 710 having a first arm 720 and a second arm 730. The first and second arms 720, 730 apply a tensioning force to an electrode material 740. Tensioning the material with a small elastic stretch ensures that the final structure can be made extremely flat, since the electrode material 740 will take on a generally planer form of its final machined mounting surface. The structure 700 can be made of aluminum and can be temporary.

The structure 700 is positioned on an air-bearing stage 750 that can be moved in the x and/or y directions in a plane perpendicular to the direction of travel of laser 760. The laser 760 can be generated by a laser scanning system 770 (e.g., apparatus 650 described above). The scanning system includes a high-precision galvanometer-type mirror system that is capable of positioning the laser spot with micron-scale precision. The laser scanning system 770 then draws the ablation pattern over the surface of the stretched film. In the same step, fiducial alignment structures can be ablated and/or cut through the film.

The electrode material 740 can be flipped over and the reverse side can be ablated to create a back side pattern, as discussed above.

Figure 8:
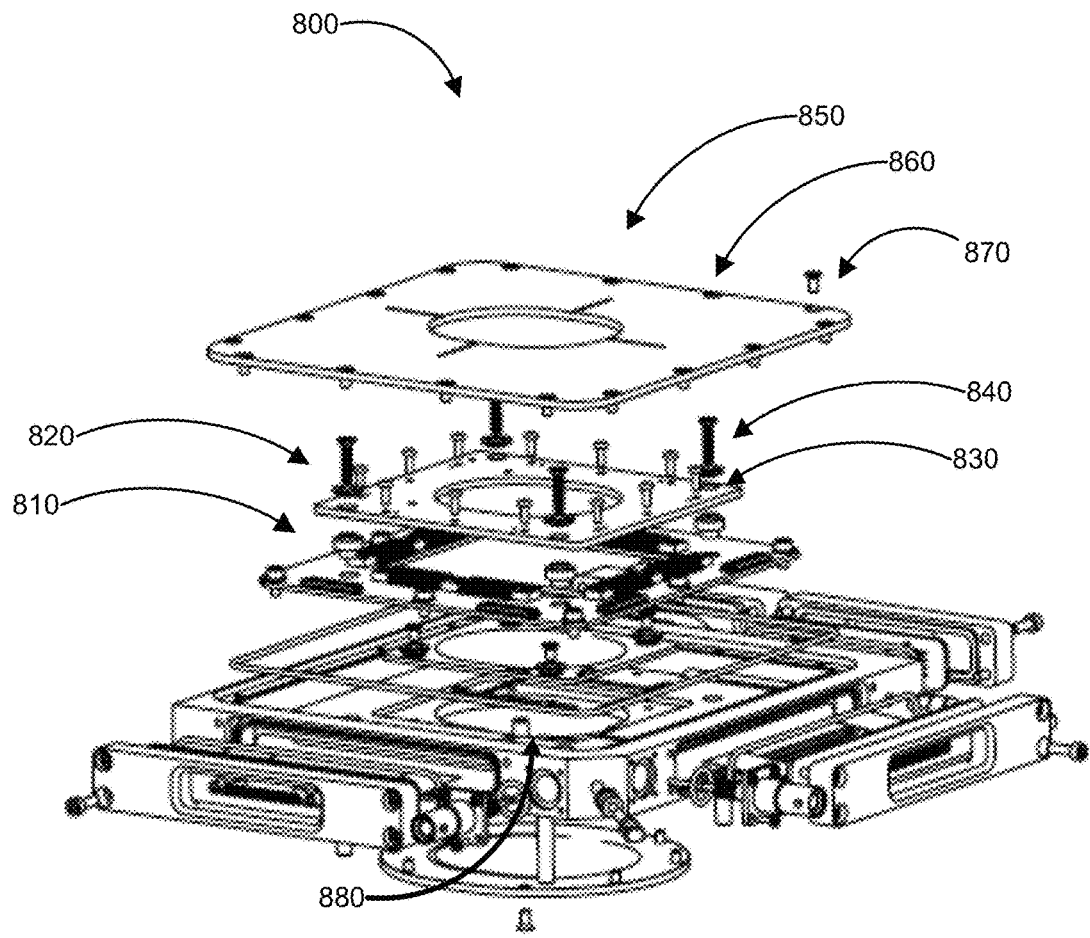
FIG. 8 is a perspective view of a pixelated detector according to an embodiment.

FIG. 8 illustrates a perspective view of a pixelated detector 800. The device 800 includes an ablated electrode material 810 bonded to a support plate 820. The support plate 820 can be a rigid insulating substrate, such as FR4 fiberglass, or a metal plate (e.g., nickel-plated aluminum), depending on the need to maintain electrical isolation on the bonded surface. The support plate 820 can be mounted on the ablated electrode material 810 utilizing fiducial structures 830 and alignment pins 840 to provide mechanical alignment between the ablated pattern and the support plate 820, which can provide an accuracy greater than about 25 microns.

The support plate 820 is disposed in an instrument case 850 using fiducial structures 860 and dowel pins 870 to maintain a high degree of mechanical alignment between the electrode pattern 810 and the instrument case 850.

A bias electrode 880 is fabricated in a similar manner, without the need for any patterning. The bias electrode 880 is mounted in the instrument case 850 with high-precision spacers to maintain a stable and accurate gas layer between the two electrode layers. The gas layer can include or can be air.

Figure 9:
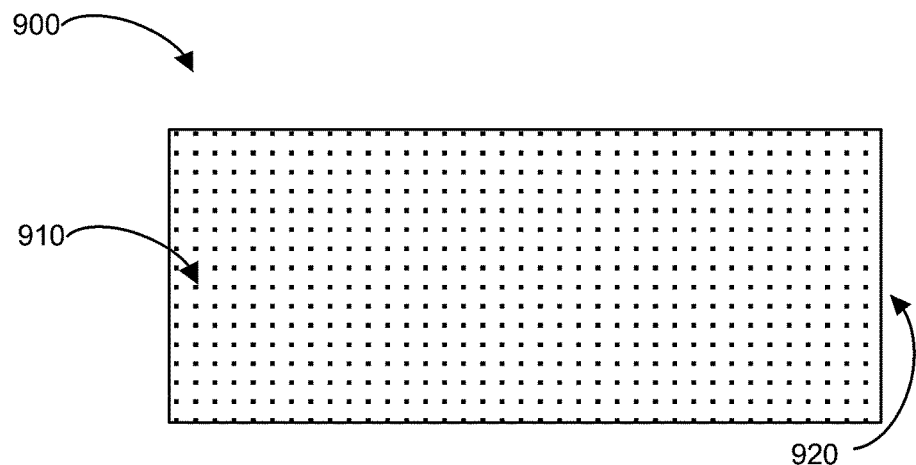
FIG. 9 is a top view of a polymer substrate having an array of holes according to an embodiment.

FIG. 9 is a top view of a polymer substrate 900 having an array of optional holes 910, according to an embodiment. The holes 910 extend through the polymer substrate 900 from an upper surface 920 to a lower surface (not shown) on an opposing side of the polymer substrate 900. The holes 910 can be created by laser machining or conventional drilling of the polymer substrate 900. In some embodiments, the polymer substrate 900 can be tensioned and/or mounted before the formation of the holes 910. A temporary mounting structure, such as mounting structure 700, can be used to provide tension and/or mount the polymer substrate 900. The polymer substrate 900 can be uncoated and can comprise polyimide. In addition, the polymer substrate 900 can be between about 10 microns and about 30 microns, between about 15 microns and about 25, about 20 microns, or about 12.5 microns thick. The holes 910 can be relatively small (e.g., between about 50 microns and about 200 microns in diameter, between about 75 microns and about 175 microns in diameter, between about 100 microns and about 150 microns in diameter, or about 125 microns in diameter) compared to the pixel size in the ablated metal surface, as described above (e.g., between about 1 mm and 5 mm in the x and/or y directions with a resolution of about 0.5 mm, 0.75 mm, or 1.0 mm per pixel), and can include multiple holes per pixel for redundancy. The size of the holes 910 can be selected to be small compared to the pixel dimensions, but relatively large compared to the thickness of the polymer substrate 900 to aid in the plating process, as described below.

Figure 10:
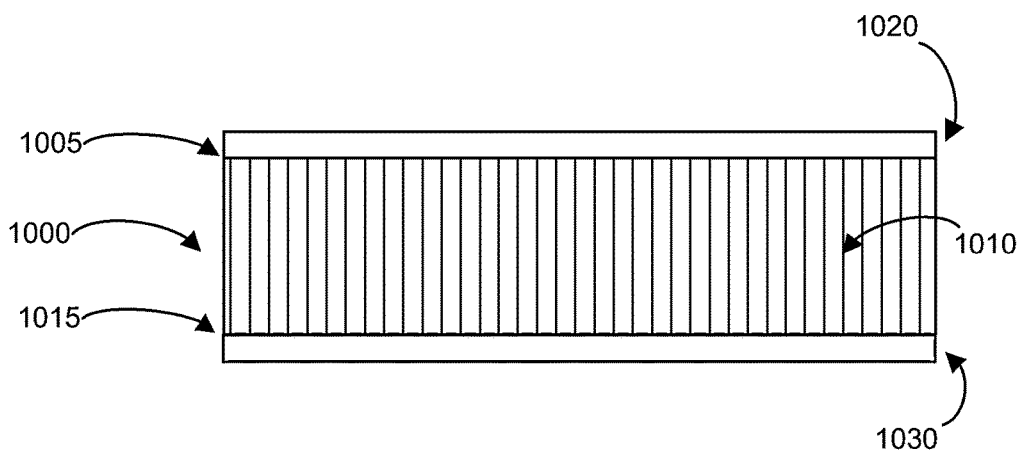
FIG. 10 is a cross-sectional view of a polymer substrate with metal layers according to an embodiment.

As illustrate in FIG. 10, a thin layer 1020 of conducting material is deposited (e.g., plated) on a front surface 1005 of polymer substrate 1000. The thin layer 1020 can have a thickness of between about 500-2000 Angstroms, such as 750 Angstroms, 1,000 Angstroms, 1,250 Angstroms, 1,500 Angstroms, or 1,750 Angstroms. The thin layer 1020 can comprise nickel. In some embodiments, the thin layer 1020 includes multiple layers of metal. Each layer can be about 100 Angstroms or less in thickness, which does not contribute significantly to the total thickness of the thin layer 1020. The thin layer 1020 can enhance adhesion of the polymer substrate 1000. For example, the layers of metal can include chromium or titanium in direct contact with the polymer substrate 1000 followed by additional layers of metal, such as nickel and/or gold. In some embodiments, a chromium layer in direct contact with the polymer substrate 1000 is coated with a titanium layer. In some embodiments, the layers of metal are selected to prevent interlayer diffusion. Alternatively, a titanium layer in direct contact with the polymer substrate 1000 is coated with a chromium layer. Chromium and/or titanium can enhance adhesion of metal layer 1020 with the polymer substrate 1000. In addition, a thin layer 1030 of conducting material is deposited (e.g., plated) on a back surface 1015 of polymer substrate 1000. The thin layer 1030 can be the same or different than the thin layer 1020. The thin layers 1020, 1030 can coat the holes 1010 to form electrically conductive "vias," which can connect pixelated electrodes on the front surface 1005 to the back surface 1015 (backside traces or sheet of metal), as described above. The pixelated electrodes and optional backside traces are formed by ablating the metal layer 1020, 1030, as described above. In some embodiments, additional metal layers (e.g., aluminum or gold) are deposited on the thin metal layers 1020, 1030 prior to ablation/fabrication.

After processing, the polymer substrate 1000 can be tensioned and bonded to a rigid support through conventional lamination, for example, using "b-staged" epoxy film, which has a relatively high radiation resistance. The use of such adhesive films can allow the parallelism of the bias and electrode planes to be maintained with high precision. The rigid support can be used for the polymer substrate 1000 regardless of the location of the traces (front side or backside) for the pixels.

The use of optional front-surface traces, as described above, in which the signal traces and the detector pixels are fabricated on the same surface, considerably simplifies the fabrication process and allows thinner ultimate constructions. However, it has the disadvantage of distorting the data as free charge in the gas gap is collected on the traces. In this sense, the detector pixels become sensitive to charge remote from their nominal positions. Fortunately, the effect of pickup on the traces can be effectively compensated.

For an incident beam of radiation with an arbitrary intensity distribution in the plane of the detector (e.g., the pixelated detector 800), one can create a distribution of electron-ion pairs in the volume of the detector that has a similar density distribution in the x-y plane (i.e., a plane perpendicular to the incident beam), and uniform distribution along the Z axis (i.e., along an axis parallel to the incident beam). For an arbitrary configuration of electrodes in the electrode plane, the charge collected on the electrode is equal to the ion-pair distribution integrated over the surface of the electrode. For a set of uniform, square, and tightly spaced pixels, the measured charge distribution collected by the pixel array accurately represents the X, Y distribution of charge density in the volume of the detector, and therefore represents the intensity distribution of the incident beam of radiation.

The existence of front surface traces introduces an error, as the traces themselves represent an effective extension of the pixels that they connect to. The collected charge corresponding to a single pixel/trace structure is now the sum of the nominal pixel, plus the contribution from the trace. The contribution due to the trace is equal to the charge density distribution integrated over the effective area of the trace. In order to recover the correct local values of the charge density distribution, we must estimate and determine the contribution from the trace, and subtract it from the total signal on that trace/pixel electrode. This can be done with good accuracy as long as the area of the trace is a small fraction of the nominal area of the pixel.

It should be noted that feature size generally means an "effective" size. In general, bare insulator is assumed not to collect charge. Instead, charge will divide between the two nearest conductors. For this reason, the effective size of any electrode feature extends half way to the adjacent electrode feature.

Figure 11:
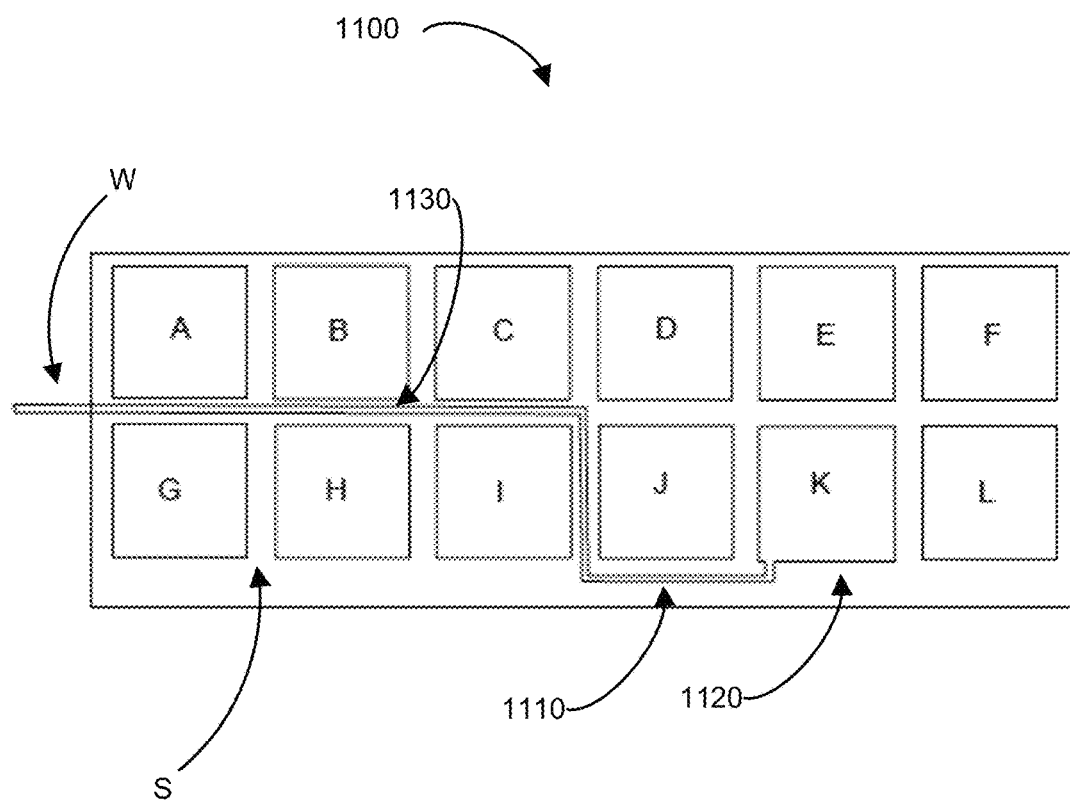
FIG. 11 is a planar view of an array of pixels according to an embodiment.

As illustrated in FIG. 11, an array of pixels 1100 is illustrated. For illustration purposes, a trace 1110 for a single pixel (K) 1120 is shown for clarity. Assume that we have pixels A through L in pixel array 1100, with corresponding current measurements IA through IL (note that traces are not shown for all pixels 1100). Once can assume a spacing between pixel centers of S and an effective trace width of W. We wish to correct the value of IK to remove the contribution of the trace area, T.

Consider the segment 1130 of the trace of length S and width W that passes between pixels B and H. The segment 1130 intercepts a current approximately equal to the local current density times the area of that trace segment. The best estimate of charge density is the average derived from the current signals on B and H.

The average charge density between B and H can be calculated as $(IB+IH)/2S2$.

The area of the trace segment between B and H can be calculated as $S*W$.

The product yields the intercepted current: $(IB+IH)W/2S$.

The total contribution along the entire "K" trace is equal to: $dIK=[(IA+IG)+(IB+IH)+(IC+II)+(II+IJ)+(IJ)]*(W/2S)$. The original value of IK can be reduced by this value. This process can be applied to all of the pixels to recreate the current distribution that would have been measured in the absence of the front-surface traces.

As can be seen, the relative size of the trace contributions scales as (W/S), so that it can be minimized by minimizing the effective area of the trace, and so its width W.

The desired measurement is the current density as a function of position. For this reason, an additional correction is required in cases in which the pixel sizes are not all equal. This situation will occur simply by the fact that the number of traces varies from place to place in the electrode pattern.

Effectively, pixel A lost some current because trace K reduced its effective area. This can be corrected by scaling up the current at A by the actual area divided by the nominal area. It is to be noted that that the combination of these two corrections results in no net change in collected current.

Take a nominal pixel size as S2. If we remove a piece at one end of width W/2, the size is now S(S−W/2) or S2−SW/2. The charge density is equal to roughly I/S2, so the current change is IAW/2S. Repeating this for pixel G, we have IGW/2S. The sum of these is (IA+IG)W/2S, which is exactly the delta subtracted from IK.

If we use the average current between the two pixels under the assumption that this represents the current density at the interface the two terms now become: (IA+IG)W/4S and (IG+IA)W/4S, which sum to (IA+IG)W/2S as before.

The corrected values can be used to prove a better estimate of the trace contributions if needed. This process may be repeated iteratively until the values converge and, therefore, the correction is known.

Figure 12:
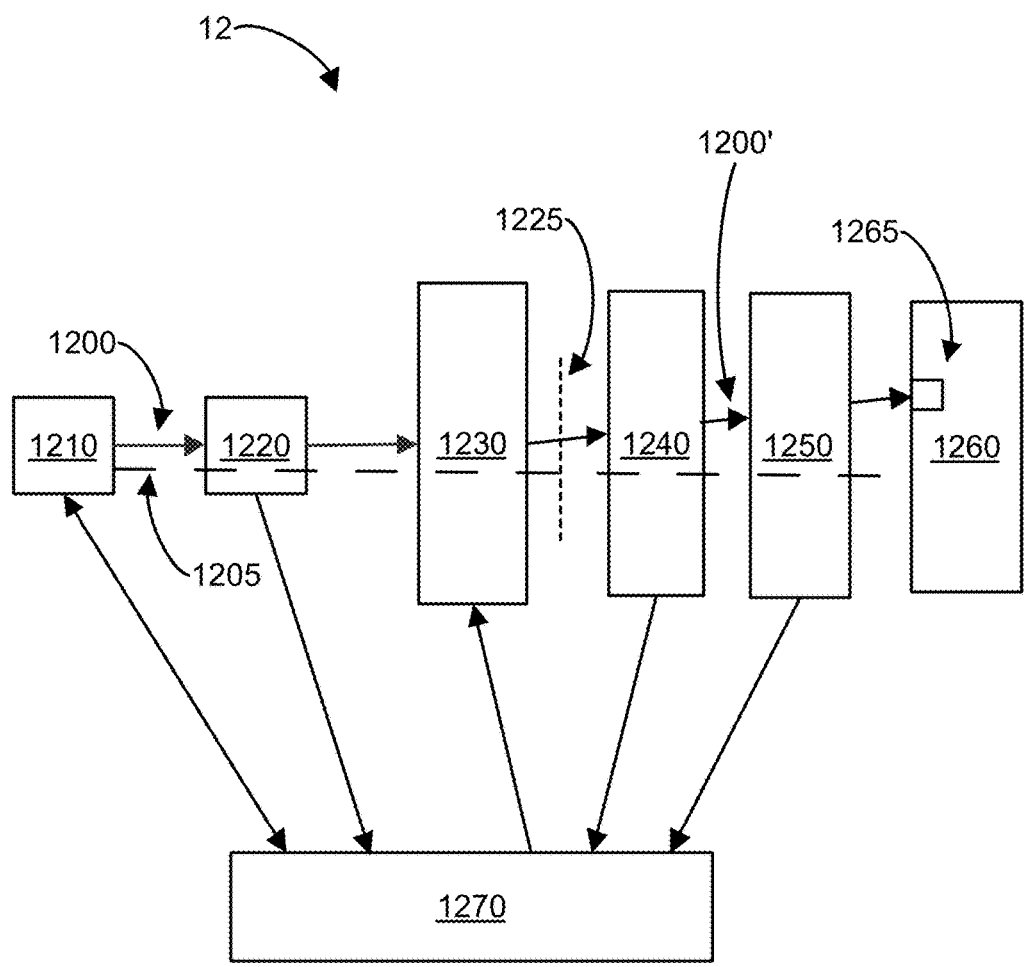
FIG. 12 is a block diagram of an embodiment of a pencil beam scanning system.

FIG. 12 illustrates a block diagram of an embodiment of a pencil beam scanning (PBS) system 12. The system 12 includes a pencil beam generator 1210, a first detector 1220, a magnetic field generator 1230, a second detector 1240, a third detector 1250, and a control system 1270. The pencil beam generator 1210 generates a charged particle pencil beam 1200 that travels, from the pencil beam generator to the first detector 1220, in a direction parallel to a reference axis 205. The charged particle pencil beam 1200 can be a proton beam or another charged particle such as nitrogen or carbon. The charged particle pencil beam 1200 has an energy (typically measured in electron volts or eV), and an intensity distribution, and a shape. In some embodiments, the energy is between 100 and 250 MeV, which can be useful for the therapeutic treatment of tumors and other conditions in a human patient. For a given time interval, the energy of the charged particle pencil beam 1200 can be generally constant. However, the energy can vary between time intervals.

As illustrated in FIG. 12, the first detector 1220 is disposed between the pencil beam generator 1210 and the magnetic field generator 1230. The first detector 1220 includes an array of elements (not shown) that are disposed crosswise in a first plane perpendicular (e.g., an x-y plane) to the reference axis 1205. The elements can be spaced apart in regular or irregular intervals in the x and y directions to define pixels. In some embodiments, elements are spaced apart about 1.0-5.0 mm in the x and/or y directions. For example, the elements can be spaced apart about 1.0 mm in the x and y directions to define pixels having about 1.0 mm of resolution. The elements detect a current formed by the charged particle pencil beam 1200 intersecting the elements, which is generally representative of the shape of the charged particle pencil beam 200. In general, the pixelated ionization chamber 1220 is thin to minimize scattering of the pencil beam 200. The first detector 2120 is configured to generate a first output signal that represents the shape and intensity distribution of the charged particle pencil beam 1200. The first detector can be the pixelated ion detector (e.g., pixelated detector 800) described above.

After passing through the first detector 1220, the charged particle pencil beam 1200 is directed by one or more magnet fields generated by the magnetic field generator 1230. The magnetic field generator 1230 can direct and/or deflect the charged particle pencil beam 1200 to form a deflected charged particle pencil beam 1200' that travels at an angle relative to the reference axis 1205 towards a model target location 1265 in the patient 1260. The model target location 1265 can correspond to a portion of a tumor in the patient 1260. In some embodiments, the magnetic field generator 1230 includes a first group of magnets and/or electromagnets for directing the charged particle pencil beam 1200 in a first direction along a plane 1225 orthogonal to the reference axis 1205 (e.g., horizontal or "x" direction) and a second group of magnets and/or electromagnets for deflecting the charged particle pencil beam 1200 in a second direction (e.g., the vertical or "y" direction). The first and second group of magnets can work together or separately to direct the charged particle pencil beam 1200 to a model target location 1265 in the patient 1260, as described above. In addition or in the alternative, the magnetic field generator 1230 can include a multipole magnet with pole pieces arranged in a symmetrical pattern centered around the undeflected axis of the charged particle pencil beam 200. Such a multipole magnet or electromagnet can direct the charged particle pencil beam 1200 in the "x" and/or the "y" direction toward the model target location 265, as discussed above. Other variations and arrangements of the magnetic field generator 1230 will be apparent to one skilled in the art.

The second detector 1240 is disposed between the magnetic field generator 1230 and the third detector 1250. The second detector 1240 can include two or more strip detector elements oriented in different directions with respect to a second plane (not shown) that is orthogonal to the charged particle pencil beam 1200. The first and second directions can be orthogonal to each other, however other relative orientations are possible, such as a 45 degree angle. The second detector is configured to detect a position (e.g., in Cartesian coordinates) in the second plane of the deflected charged particle pencil beam 1200'.

Figure 13:
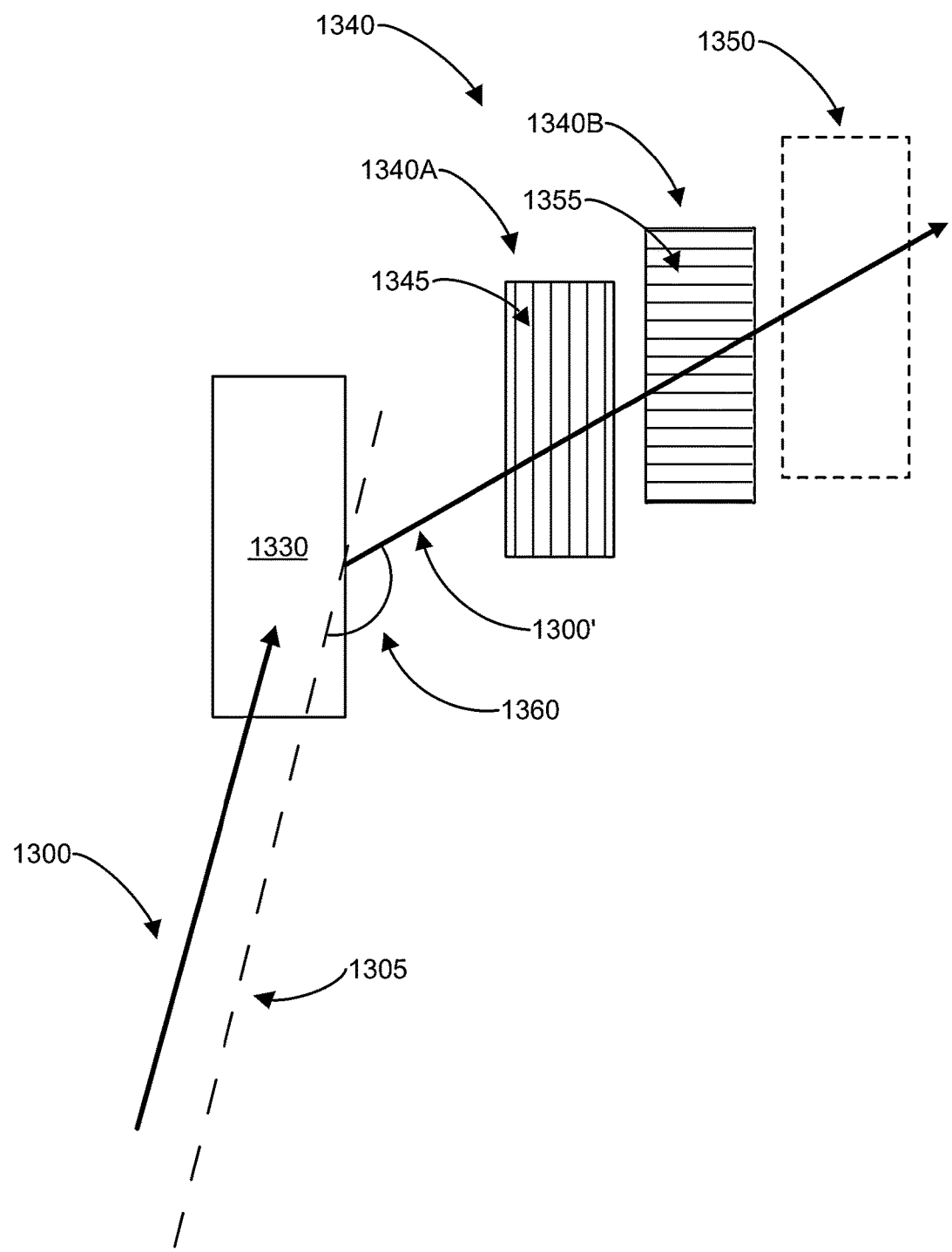
FIG. 13 is an embodiment of a detector system for a pencil beam scanning system.

FIG. 13 illustrates an embodiment of the second detector 1240 illustrated in FIG. 12. Second detector 1340 includes a first strip detector element 1340A and a second detector element 1340B that are oriented to be parallel to a second plane 1350. The second plane 1350 is orthogonal to a reference axis 1305, which is parallel to a direction of travel of a charged particle pencil beam 1300. The first strip detector element 1340A includes a plurality of strips 1345 oriented in a first direction (e.g., a vertical direction) with respect to the second plane 1350. The second strip detector element 1340B includes a plurality of strips 1355 oriented in a second direction (e.g., a horizontal direction) with respect to the second plane 1350. As illustrated in FIG. 13, the second direction is orthogonal to the first direction. However, other relative orientations are possible.

Figure 14:
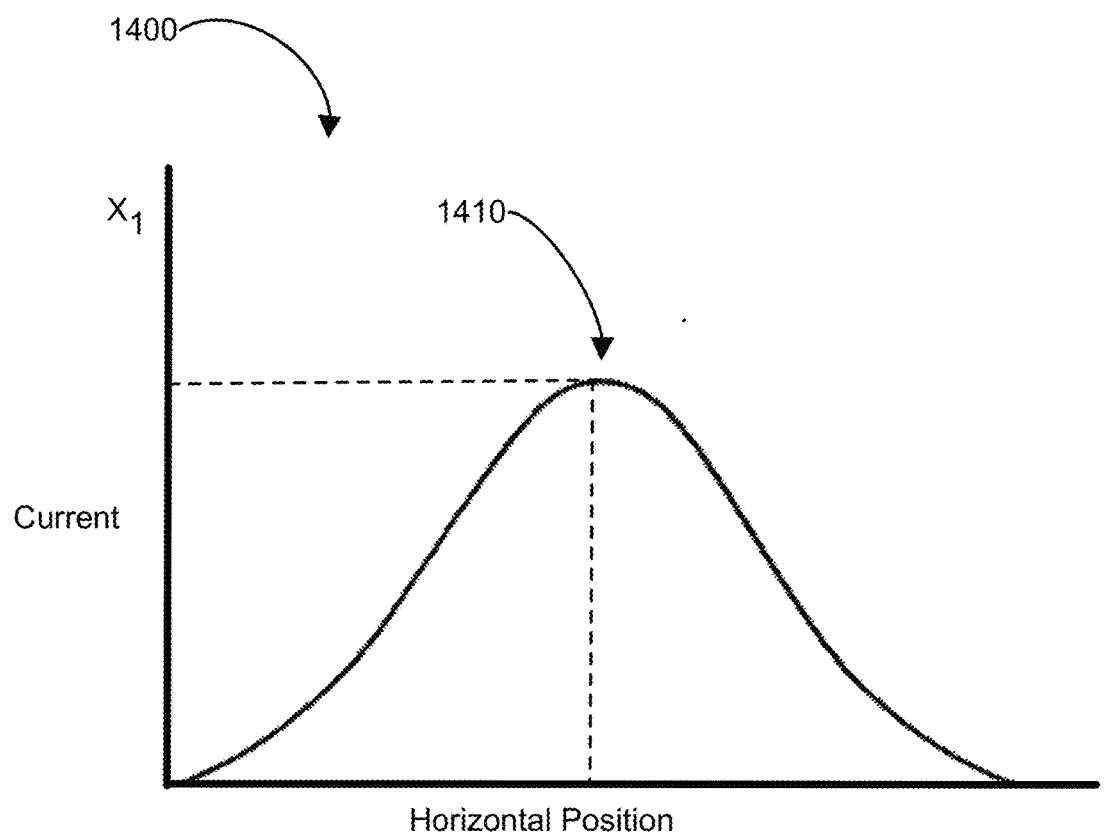
FIG. 14 is an illustration of current distribution in a detector system for a pencil beam scanning system according to an embodiment.

In operation, a magnetic field generator 1330 deflects the charged particle pencil beam 300 to form a deflected charged particle pencil beam 1300'. The deflected particle pencil beam 1300' is deflected at an angle 1360 with respect to the reference axis 3105. The deflected particle pencil beam 1300' then passes through the second detector 1340. The first strip detector element 1340A detects the electrical current on each strip 1345 generated by the deflected particle pencil beam 1300'. With reference to FIG. 14, the distribution of electrical current 1400 across the vertical strips 1345 is representative of a centroid position 1410 of the deflected particle pencil beam 1300' along the axis perpendicular to the direction of direction of the strips 1345 (i.e., a coordinate $x_1$ in the horizontal or "x" direction). For example, a series of vertical strips in the "y" direction will yield a current distribution 1400 representative of the centroid of the deflected particle pencil beam 1300' along the horizontal or "x" direction.

Figure 15:
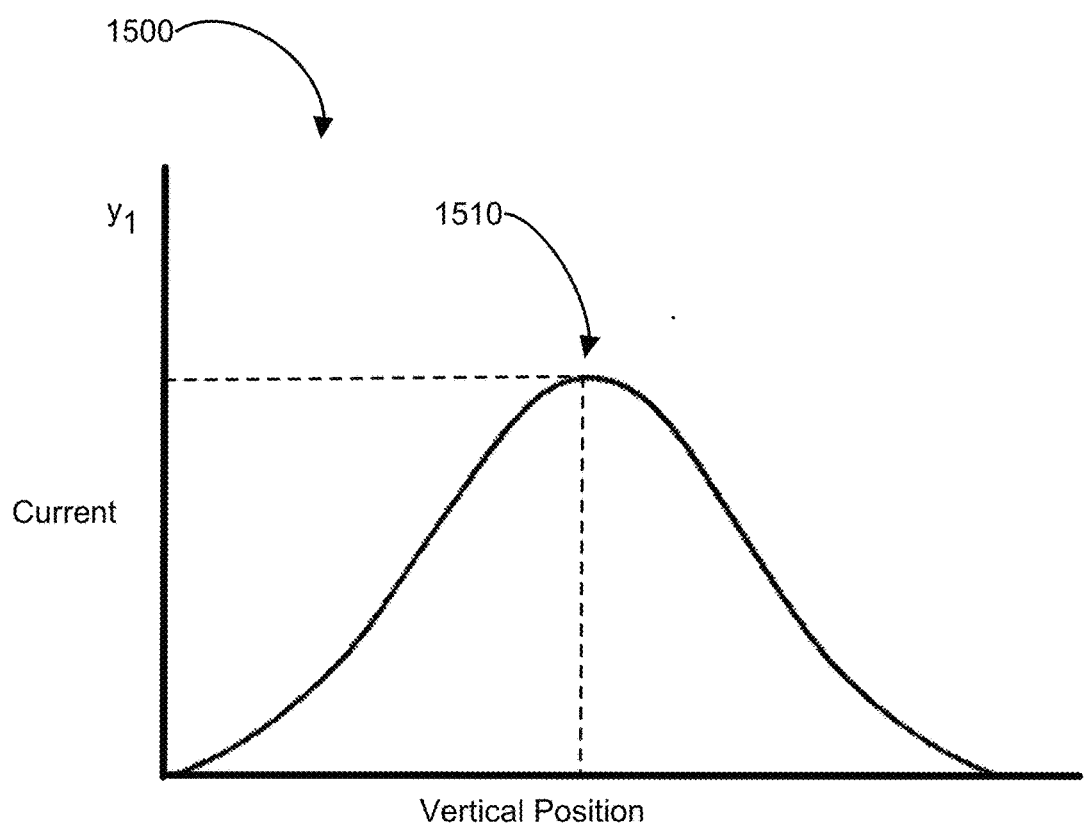
FIG. 15 is an illustration of current distribution in a detector system for a pencil beam scanning system according to an embodiment.

Next, the deflected particle pencil beam 1300' passes through the second strip detector element 1340B, which detects the electrical current on each strip 1355 generated by the deflected particle pencil beam 1300'. With reference to FIG. 15, the distribution of electrical current 500 across the horizontal strips 355 is representative of a centroid position 1510 of the deflected particle pencil beam 1300' along the axis perpendicular to the direction of direction of the strips 1355 (i.e., a coordinate $y_1$ in the vertical or "y" direction). For example, a series of horizontal strips in the "x" direction will yield a current distribution 1500 representative of the centroid of the deflected particle pencil beam 1300' along the vertical or "y" direction.

Returning to FIG. 12, the second detector 1240 is configured to generate a second output signal that represents the distribution of electrical current (e.g., distributions 1400 and 1500) measured by each strip detector element (e.g., strip detector elements 1340A, 1340B, 1340*n*). The centroid position coordinate measurements of the first and second electrode assemblies represent a first position (e.g., $(X_1, Y_1)$ in Cartesian coordinates) of the deflected particle pencil beam 1300'. In some embodiments, the second detector 1340 is a pixelated detector or a series of pixelated detectors.

Figure 16:
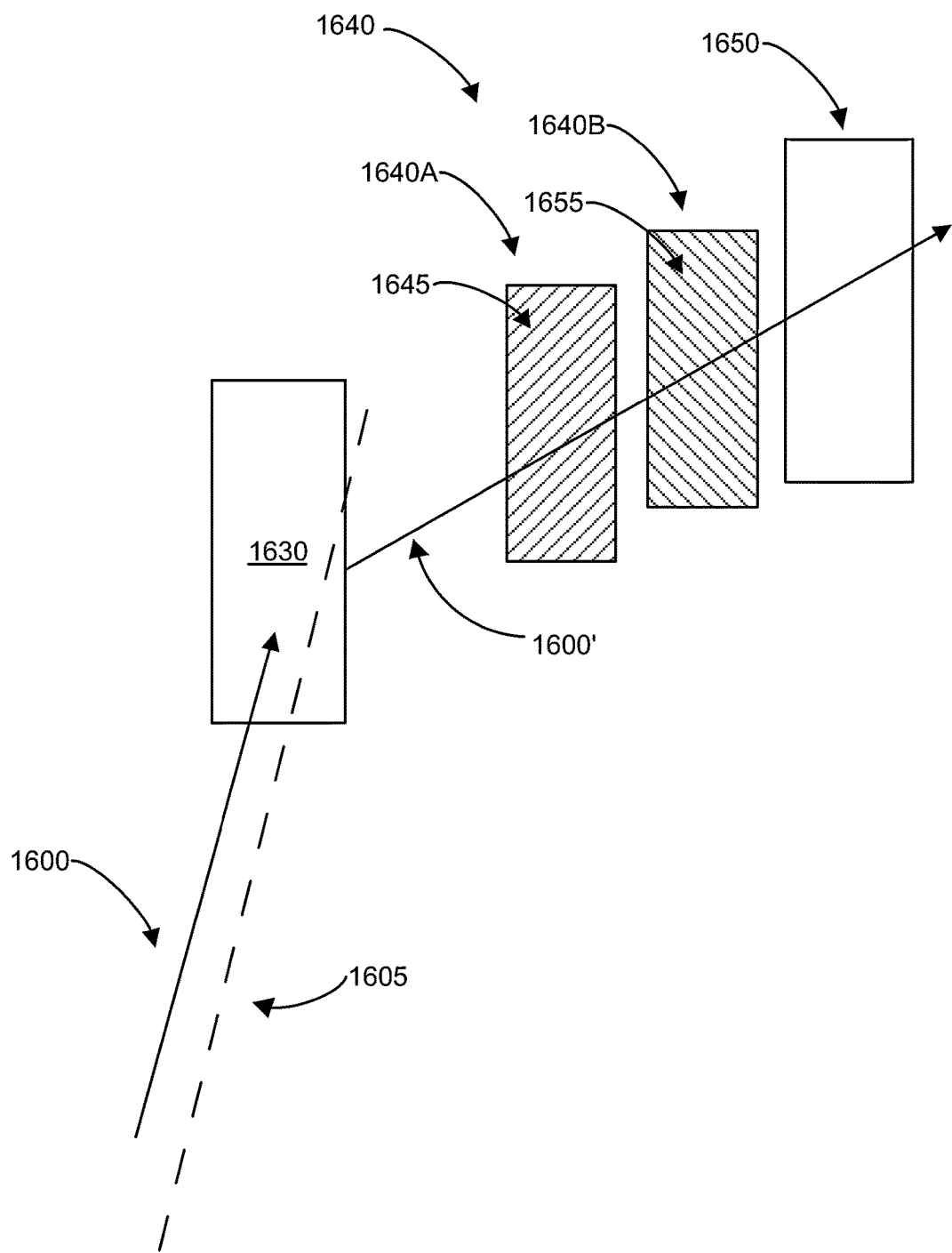
FIG. 16 is an embodiment of a detector system for a pencil beam scanning system.

The third detector 1250 can be the same or different than the second detector 1240. For example the third detector 1250 can have additional or fewer strip detector elements. Similarly, the strip detector elements can have the same or different orientations than the first and second strip detector elements 1340A and 1340B, respectively, as illustrated in FIG. 13. An embodiment of the third detector 1250 is illustrated in FIG. 16. The third detector 1640 includes a first strip detector element 1640A and a second strip detector element 1640B. As illustrated in FIG. 16, the strips 1645 in the first detector element 1640A are offset by about 45 degrees from the strips 1345 in the first detector element 1340A, as discussed above. Similarly, the strips 1655 in the second detector element 1640B are offset by about 45 degrees from the strips 1355 in the second detector element 1340B, as discussed above.

Returning to FIG. 12, the third detector 1240 is configured to generate a third output signal that represents the distribution of electrical current (e.g., distributions 1400 and 1500) measured by each strip detector element (e.g., strip detector elements 1340A, 1340B, 1340*n*). The centroid position coordinate measurements of the first and second electrode assemblies represent a second position (e.g., $(X_2, Y_2)$ in Cartesian coordinates) of the deflected particle pencil beam 1300'. In some embodiments, the second detector 1340 is a pixelated detector or an array of pixelated detectors.

The controller 1270 comprises a processor (e.g., a microprocessor, a graphics processing unit, etc.) and receives the first output signal from the first detector, the second output signal from the second detector, and the third output signal from the third detector. The controller 1270 compares the actual data received in the output signals with target data and/or a treatment plan. Based on the comparison, the controller 1270 generates an intensity control signal to send to the pencil beam generator 1210 and a target location control signal to send to the magnetic field generator 1230. In some embodiments, the controller 1270 generates a signal to stop the charged particle beam generator 1210 if the actual data is not within a tolerance of the target data, as described below.

Figure 17:
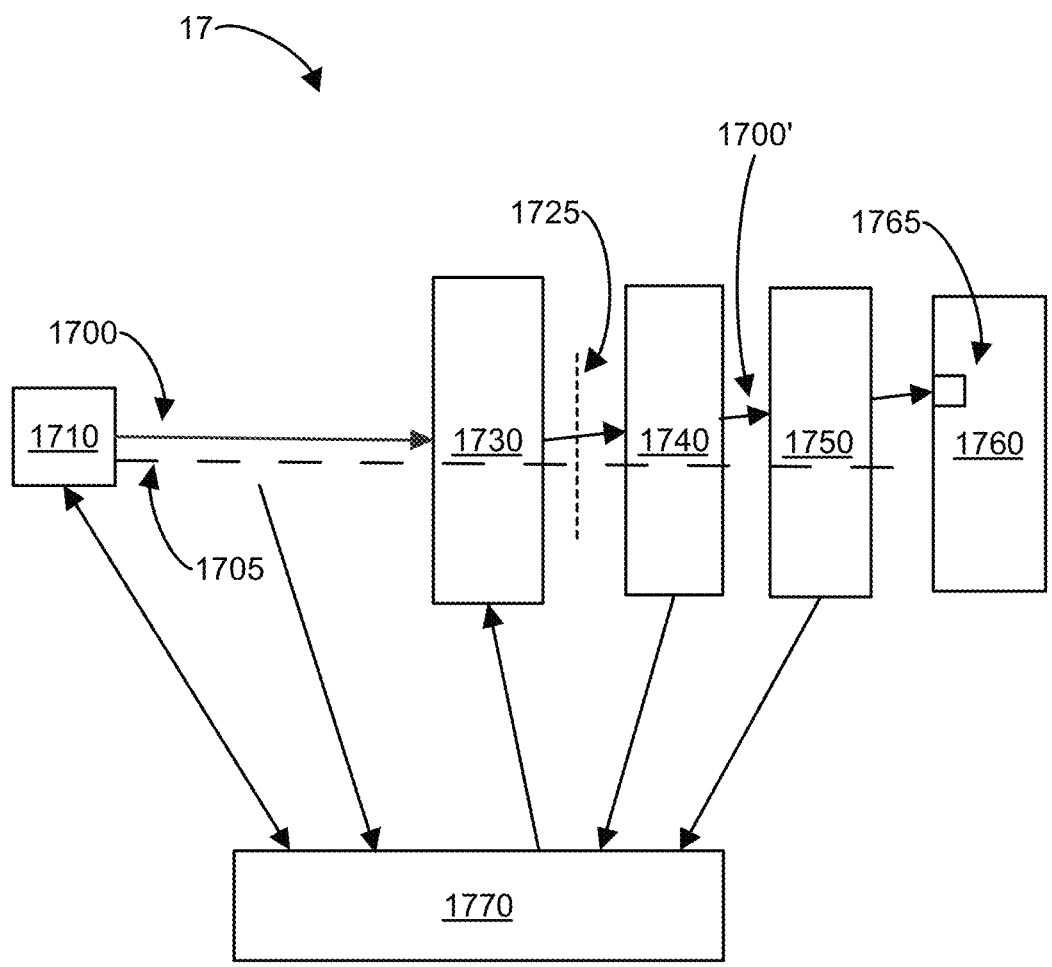
FIG. 17 is a block diagram of an embodiment of a pencil beam scanning system.

FIG. 17 illustrate another embodiment of a block diagram pencil beam scanning (PBS) system 17. The system 17 includes a pencil beam generator 1710, a magnetic field generator 1730, a second detector 1740, a third detector 1750, and a control system 1270. In this embodiment, the second detector 1740 and/or the third detector 1750 is a pixelated detector as described above. No detectors are needed between the pencil beam generator 1710 and the magnetic field generator 1730, although such detector can optionally be disposed at such location.

Figure 18:
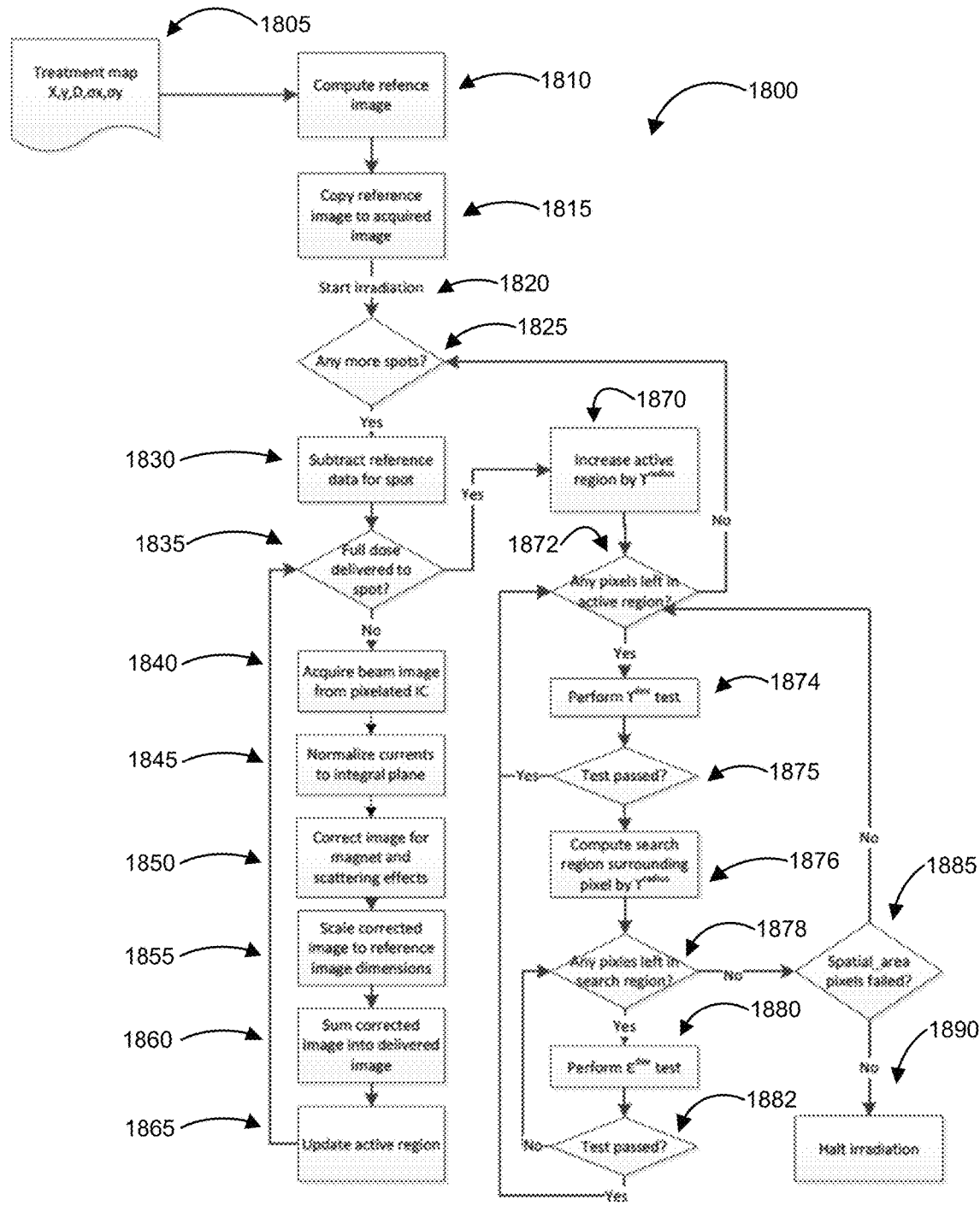
FIG. 18 is a flow chart for real-time verification and control of charged particle pencil beam therapy according to an embodiment.

FIG. 18 illustrates an embodiment of a flow chart 1800 for real-time verification and control of charged particle pencil beam therapy. The flow chart includes a verification technique similar to the gamma dose distribution. Gamma distribution tests are well known in the art as a method of statistically comparing dosage distributions. See, e.g., Jiang, S., et al., "On Dose Distribution Comparison," Phys. Med. Biol. 51 (2006) 759-776, which is hereby incorporated herein by reference. Other statistical techniques can be used, as known in the art, but the gamma test is illustrated due to its popularity in the industry.

In step 1805 a controller or other computer system receives a treatment map that corresponds to a model dose distribution, including shape and location, of a tumor in the patient. The treatment map can be received from a database, a host computer, or a removable media. Alternatively, the treatment map can be stored locally on the controller or computer system described above. The treatment map includes a series of energy "layers" that correspond to the three-dimensional depth of the tumor (e.g., a higher energy is needed to reach further into the tumor). On each energy layer the treatment plan consists of data representing a list of spots with the following information for each spot:

x  x coordinate at isocenter (millimeters)
    y  y coordinate at isocenter (millimeters)
    D  target therapeutic dose (Proton count or monitor units)
    σx beam sigma in the x-axis (millimeters)
    σy beam sigma in the y-axis (millimeters)

As discussed above, the "x" and "y" coordinates refer to the model target coordinates for the charged particle pencil beam to provide a target therapeutic dose D to the patient (e.g., a location of a tumor). The "x" and "y" coordinates are defined by a reference plane (e.g., plane 1225) that is orthogonal to a reference axis (e.g., reference axis 1205), which is parallel to the direction of travel to the charged particle pencil beam. The numbers σx and σy refer to the standard deviation of the x and y coordinates assuming that the charged particle pencil beam has a Gaussian distribution in both the x and y directions. As such, the numbers σx and σy are representative of the "width" or "size" of the charged particle pencil beam across the reference plane.

In step 1810, the controller computes a reference matrix from the treatment map data received in step 1805. In some embodiments, the reference matrix is calculated by a server or other computer. The reference matrix can be a rectilinear grid with a resolution and size adequate to store information for the entire irradiated field. As will be recognized by one skilled in the art, various resolutions can be used such as the lower of σx/3 and σy/3 (i.e., min {σx/3, σy/3}) or other fractions of σx and/or σy. For example, a charged particle pencil beam with a beam sigma of 6 mm in the x and y directions and a target scan area at isocenter of 300×400 mm, an array size of 150×200 pixels could be used. Since the treatment plan is generated based on the assumption that the charged particle pencil beam is Gaussian, the information from the treatment plan is used to construct the reference image that represents the target spatial dose distribution for the energy layer. This can be formed by superimposing the sum of the computed 2D Gaussians (e.g., σx and σy) for each spot. Each spot's contribution to the reference image is also maintained as a separate list of {xref, yref, Dref} for later use during the real-time computations. The x and y positions are mapped to xref and yref by scaling to the matrix size, and the dose D is converted to Dref in charge units using the calibrated dose information from the QC process. The dose calibration in the QC step is done by placing a fiducial 3D device at isocenter, such as a water phantom, then running beams at various intensities (dose rates) and energies and collecting data. The data is used as a reference during clinical treatment, such as through a table look-up or a functional relationship between the position, intensity, and energy.

In another embodiment, a three dimensional reference image is generated using additional information from the treatment plan, including the Bragg curves used for the particular treatment. The third dimension has the same spatial resolution of the first two dimensions and has size (depth) large enough to represent the entire irradiated volume. In another embodiment, the two dimensional or three dimensional reference matrix is supplied directly by the treatment planning system, supplying separately the individual contributions for each spot.

In step 1815, the controller copies the values of the reference matrix to an acquired matrix, which can have the same size and resolution as the reference matrix. The gamma distribution method requires that the reference and actual distribution matrixes be complete (e.g. all pixels filled in as if the treatment was complete), so that the reference data and the acquired data can be compared for every pixel. To perform a gamma distribution analysis as the treatment progresses with incomplete actual data, the acquired data (the history) can be combined with the reference information for all non-irradiated spots (the model) to get the complete image needed for calculation of the gamma distribution.

In step 1820, patient treatment using a charged particle pencil beam (e.g., a proton pencil beam) begins. Processing continues for each spot in the treatment map, as long as there are spots remaining, as indicated in step 1825. For each spot processed, the reference data for that spot is subtracted from the acquired matrix in step 1830. In other words, the reference data is removed or "zeroed out" from the acquired matrix for the next spot to be treated. This allows the irradiated pixel data caused by the spot irradiation to be populated by the actual data as treatment proceeds, as described below.

In step 1835, a determination is made whether the target therapeutic dose of charged particle therapy has been delivered to the spot. In general, the therapeutic dose is a function of the intensity and duration of the charged particle pencil beam. When treatment on a new spot begins, the dose delivered to that spot will be zero. If the total target therapeutic dose has not been delivered to the spot, treatment of the spot continues.

In step 1840, an image of the charged particle pencil beam is collected from the pixelated detector (e.g., the first detector 1220). The image represents the spatial charge distribution of the beam, returned as a two dimensional matrix of beam currents. The intensity distribution can be measured by the current densities (current in each pixel divided by area of such pixel) across the beam shape. In general, the shape and intensity distribution are measured over a time interval that is a fraction of the total time needed to provide the planned therapeutic dosage of the charged particle pencil beam at a given spot. In some embodiments, a cumulative shape and intensity distribution are measured over the total dosage time.

In optional step 1845, the current in the pixelated detector can be normalized to a current measurement made by an integral plane detector near the treatment isocenter. As understood by one skilled in the art, an integral plane detector is frequently used to determine the total intensity of the charged particle pencil beam. In this case it may be desirable to "normalize" the pixelated array currents to this total measured value, thereby using the pixelated array only as a measurement of the beam current distribution. To normalize the current measured by the pixelated detector with the current measured by the integral plane detector, each pixel's current is divided by the total of the current for all pixels to calculate a percentage contribution of each pixel to the total current measured by the pixelated detector. The percentage contribution of each pixel is then multiplied by the total current measured by the integral plane to calculate the normalized current for each pixel. However, it is noted that the pixelated detector currents are normally adequate to characterize the dose distribution.

In optional step 1850, the beam image measured by the pixelated detector can be corrected for magnetic field and/or scattering effects. The beam shape as measured by the pixelated detector (e.g., detector 800) at the scan magnet entrance may not be exactly what is delivered at the patient isocenter, due to possible scan magnet aberrations and beam scattering. Examples of magnet aberrations can include size and rotational effects. These "defects" can be quantified in advance during a test or quality-control run and can then applied to the beam image data, for example, as the data is collected. For example, a fiducial 2D or 3D detector device can be placed at isocenter. In the test run, beams of the charged particle beam can be emitted at varying energies at various scan locations in the x-y plane (i.e., locations perpendicular to the direction of travel of the charged particle beam before deflection). The shape of the beam measured by the pixelated IC is then compared to the shape measured by the QC fiducial detector device, and corrections such as theta (rotation) and zoom (size) can be calculated. These corrections can be negligible, a function of the scan position in the x-y plane, a function of the beam energy, a function of the gantry angle, and/or other variable. Such a process is similar to what is done in the industry to characterize the calibrations of the scanning magnet amplifier control voltage and positions in the x-y plane, and to the measured intensity in the IC devices to the real clinical dose.

In step 1855, the image data (or corrected and/or normalized image data if steps 1845 and/or step 1850 are performed, respectively) from the pixelated detector is scaled to the resolution and dimensions of the acquired matrix if the pixelated detector has a different resolution and dimensions than the acquired matrix. In general, the pixels in the pixelated detector will have a lower resolution than the pixels or spots in the acquired matrix and, therefore, the data from the pixelated detector will need to be scaled (e.g., expanded) to "fit" into the acquired matrix. In some embodiments, the acquired matrix has a resolution that is an even multiple of the pixels or spots in the pixelated detector to allow for more rapid calculations.

In step 1860, the image data (or corrected and/or normalized image data if steps 1845 and/or step 1850 are performed, respectively) is summed into the acquired matrix. To sum the image data, the centroid position of the image shape at the isocenter plane (plane orthogonal to direction of undeflected charged particle beam) is determined. After the beam is deflected by a magnetic field generator (e.g., magnetic field generator 1330), two detectors measure the x and y centroid coordinates of the charged particle pencil beam at two different locations, as discussed above. Using the two pairs of centroid coordinates (e.g., (x1, y1), (x2, y2)), the centroid position at isocenter can be calculated through interpolation of the measured centroid coordinates. As discussed above, the centroid coordinates are provided with respect to a reference plane (e.g., an x-y plane) that is orthogonal to a reference axis, which is parallel to the direction of travel of the undeflected charged particle pencil beam. After interpolation, the image data is summed into the centroid position in the acquired matrix. It is noted that the interpolation portion of this step is optional if the acquired matrix has the same resolution as, or an even multiple of, the pixelated detector. By summing the image data into the acquired matrix, the shape, intensity distribution, and location of the charged particle pencil beam is superimposed in the acquired matrix. This can create a more accurate measurement of the dose and dose distribution of the charged particle pencil beam treatment.

Figure 1:
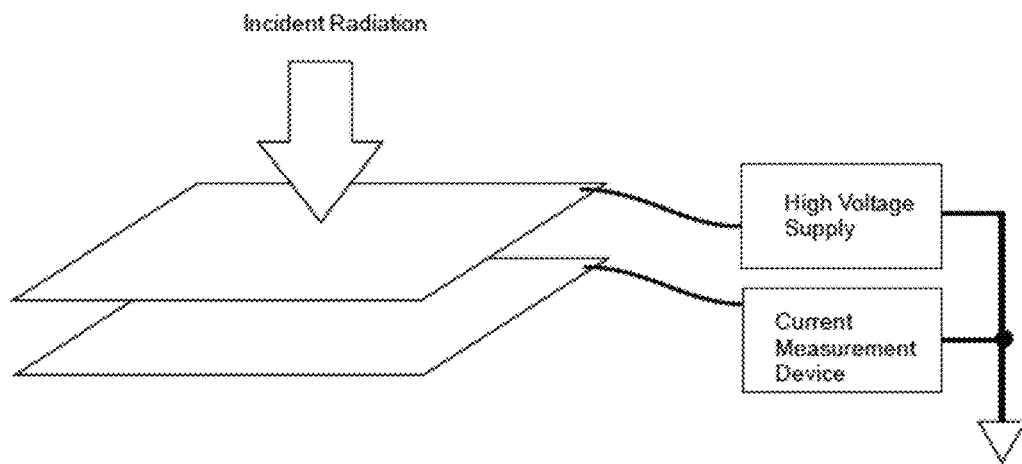
FIG. 1 is a planar view of an exemplary transmission ion chamber detector.
Figure 2:
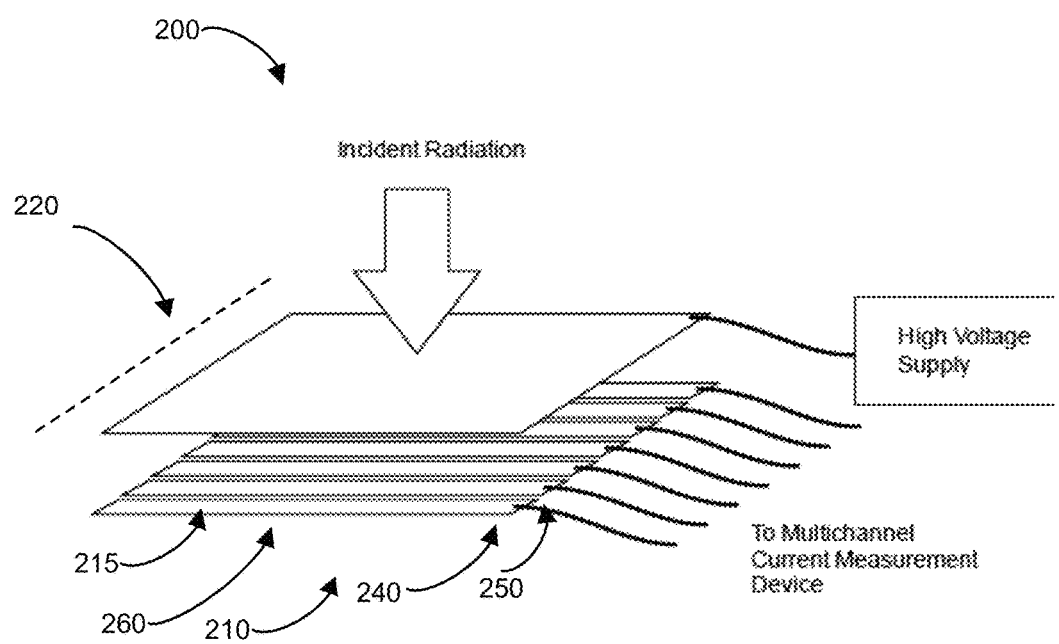
FIG. 2 is a planar view of an exemplary transmission ion strip detector.
Figure 3:
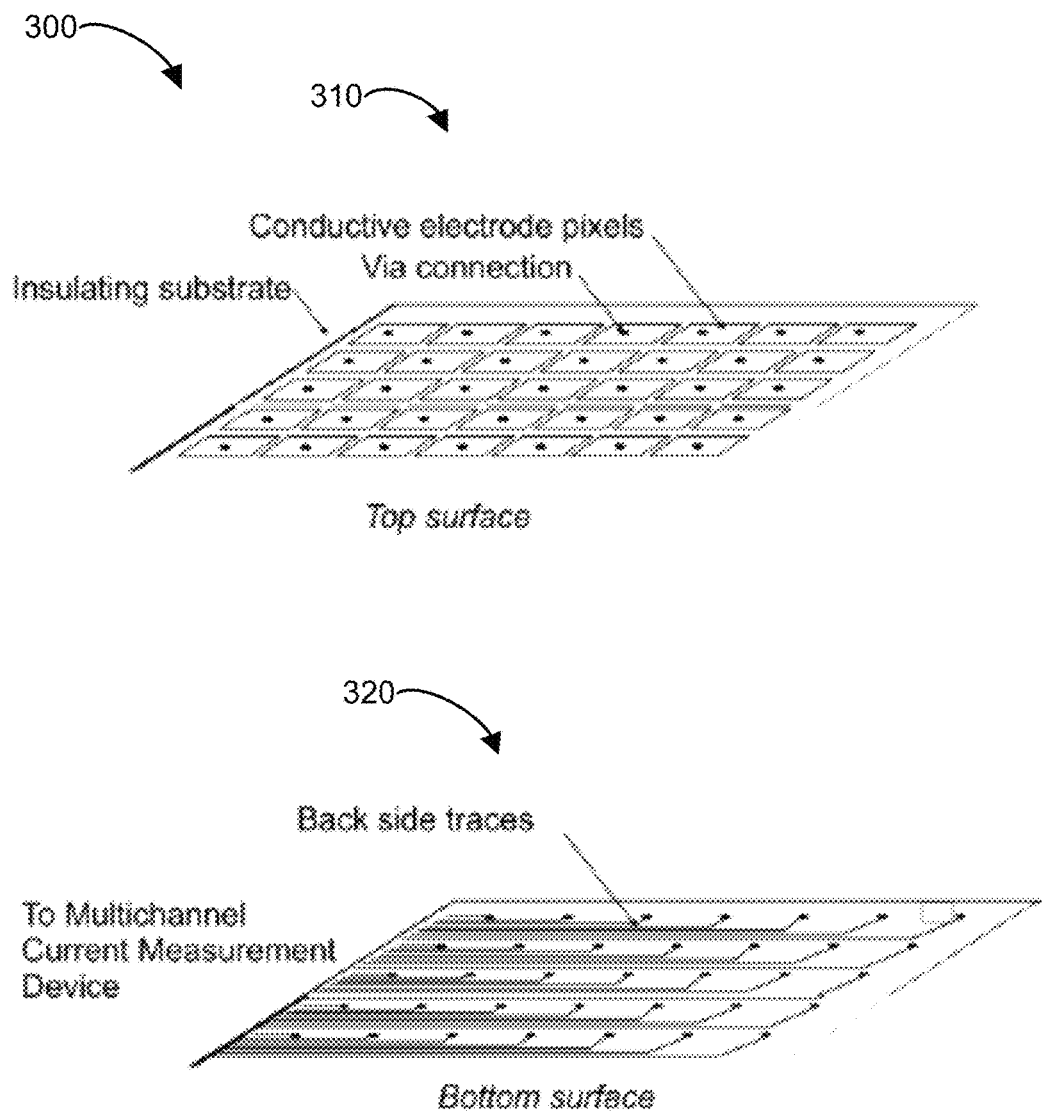
FIG. 3 is a planar view of an exemplary pixelated transmission ion chamber detector.
Figure 4:
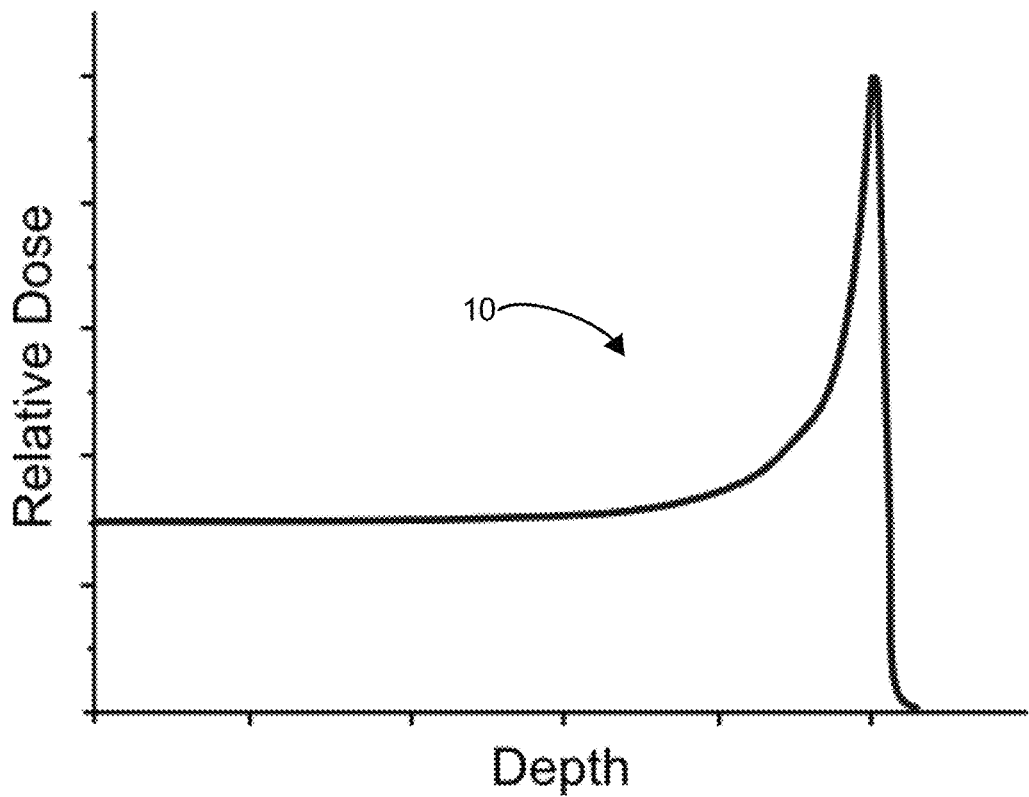
FIG. 4 is an exemplary Bragg curve.

In some embodiments, the acquired matrix includes a depth dimension determined by Bragg curve data (see FIG. 4) for the charged particle pencil beam. The Bragg curve data can be refined by incorporating information about the target area, such as CT scan density.

In step 1865, an active region of the acquired matrix is updated. During therapy of a spot, each time interval of the image data is summed into the corresponding pixels in the acquired matrix centered around the isocenter position (in the isocenter plane) as determined by the interpolation of x,y data from the detectors after the magnet, as discussed above. As this occurs an "active region" is maintained by the software that defines the region where pixels have been modified in the acquired image. In general, this is the maximum and minimum x and y coordinates affected during irradiation of the spot.

After the active region is updated in step 1865, the flow chart proceeds back to step 1835 to determine whether the target therapeutic dose of charged particle therapy has been delivered to the spot. As discussed above, steps 1840, 1845, 1850, 1865, and 1860 can be performed for a time interval that is a fraction of the time needed to deliver the target therapeutic dose of charged particle therapy to a given spot. When such a short time interval is used, the loop of steps 1835, 1840, 1845, 1850, 1865, and 1860 proceeds in real time until the total dosage time has been reached. Alternatively, steps 1840, 1845, 1850, 1865, and 1860 are performed once after the total dosage is delivered in which case data from the pixelated detector and the two detectors after the magnet can be saved at a time interval that is a fraction of the time needed to deliver the target therapeutic dose of charged particle therapy to a given spot.

The active region computed in 1865 results from keeping track of where in the total surface the beam actually strikes. Step 1870 expands this region on all sides in order to force checks for nearby pixels that are $Y^{radius}$ away. The reason this is done is that the evaluated status of these outliers may be affected if they had previously passed because of the secondary $\epsilon^{dev}$ test in step 1880, which uses pixels in the active region. While the gamma technique relates to the entire surface, the active region is used to reduce computational time by limiting checks only to the affected regions. In some embodiments, a gamma technique is applied to the irradiated volume. In this case the Bragg curve data is incorporated in the image data in the acquired matrix, in which case the active region is expanded across all 3 dimensions of the volume.

In step 1872, each pixel in the expanded active region is evaluated to confirm that its dose has been adequately delivered according to the reference specification or matrix. The primary gamma deviation in test 1874 is applied, and if needed, a secondary epsilon deviation in test 1880.

In step 1874, a gamma deviation ($Y^{dev}$) test is performed for each pixel in the active region. The absolute value of the difference between the pixel value in the reference and the acquired images is compared to a specified percentage ($Y^{dev}$) of the reference pixel value. While 2% is typically the accepted deviation value for this analysis, this percentage can be changed by an operator or medical physicist since the parameter is a settable variable. The pixel passes the gamma deviation ($Y^{dev}$) test if the deviation is under this value.

In step 1875, if the pixel passes the gamma deviation ($Y^{dev}$) test then the pixel is considered as passed and no further evaluation for the pixel is needed. If this is the case evaluation then proceeds to the next pixel in step 1872. If the test fails, the process proceeds to a secondary check beginning at step 1876.

The secondary check is computed on the region immediately surrounding the pixel, defined by a radius $Y^{radius}$. This region is determined by step 1876, and can be a two-dimensional or a three-dimensional region.

In step 1878, each pixel in the region defined in step 1876 is passed on to the secondary check until there is none left, in which case the pixel has failed all tests, in which case processing proceeds to step 1885.

For each pixel computed in step 1876, a secondary $\epsilon^{dev}$ test is performed. This test is similar to the $Y^{dev}$ test in step 1874 except that a typically smaller percentage tolerance $\epsilon^{dev}$ is used instead of the $Y^{dev}$ used in step 1874. The secondary $\epsilon^{dev}$ test generally is used to determine if any pixel in the region surrounding the pixel of interest "very closely" matches the pixel's reference dose requirement. The primary $Y^{dev}$ test (step 1874) allows a more relaxed (2% typical) tolerance. In contrast, an $\epsilon^{dev}$ of 0.25% or less can be used in step 1880. It is noted that $\epsilon^{dev}$ can be set by an operator or medical physicist depending on the desired tolerance level.

In step 1882, if the test in step 1880 passes for the given pixel undergoing the secondary epsilon test, $\epsilon^{dev}$ test, (i.e., within a radius of $Y^{dev}$ from the pixel that failed the gamma test), then the primary pixel being evaluated is considered passed, and processing can continue with the next pixel in step 1872. Otherwise the secondary test is applied to the next pixel in the region defined by step 1876.

If none of the pixels pass the $\epsilon^{dev}$ test in step 1880, a spatial area pixel failure test is performed in step 1885. The spatial area pixel failure test has a tolerance for the number of pixels that can fail within a spot (or volume if Bragg curve data is included, as described above) to stop treatment. In other words, the treatment (irradiation) will stop if more than a certain number (set by the tolerance) of pixels are "bad." The tolerance can be user defined.

If the spatial failure test in step 1885 fails (i.e., there are more "bad" pixels than the tolerance level), the treatment will halt in step 1890. In some embodiments, a graphical representation (e.g., a contour map) of the pixel failures and/or the treatment distribution is presented to an operator for diagnosing whether a meaningful treatment error has occurred. If the spatial failure test in step 1885 passes (i.e., there are fewer "bad" pixels than the tolerance level), the flow chart returns to step 1872 to determine if any pixels remain in the active region for testing.

In one embodiment, the flowchart 1800 can be described by the following pseudo code:

```
// DATA ACQUISITION
foreach spot
{
    Subtract reference image contribution for spot from delivered image
    foreach timeslice
    {
        Acquire data from pixelated IC
        Correct data for magnet and scattering aberrations
        Scale data to reference image dimensions
        Add data into delivered image using interpolation
        Record minimum and maximum extents in the delivered image
    }
    Expand minimum and maximum extents to account for all affected
    pixels
}
// GAMMA-INDEX COMPUTATION
foreach (x,y,D) grid point in minimum and maximum extents
{
    // Perform first pass to see if dose within preset gamma tolerances
    delta = delivered[x,y]- reference[x,y]
    if |delta| < (Y^dev/100 * reference[x,y])
        continue, pixel is ok
    // Perform second pass to see if dose in surrounding area
    // is within preset secondary tolerance
    Compute distance set (xg,yg,Dg)
    foreach distance set(xg,yg,Dg)
    {
        delta = delivered[xg,yg] − reference[x,y]
        If (|delta| < ε^dev)
        {
            passed = true;
            break;
        }
        if (NOT passed)
        {
            Pixel FAILED criteria
        }
    }
}
```

Figure 19:
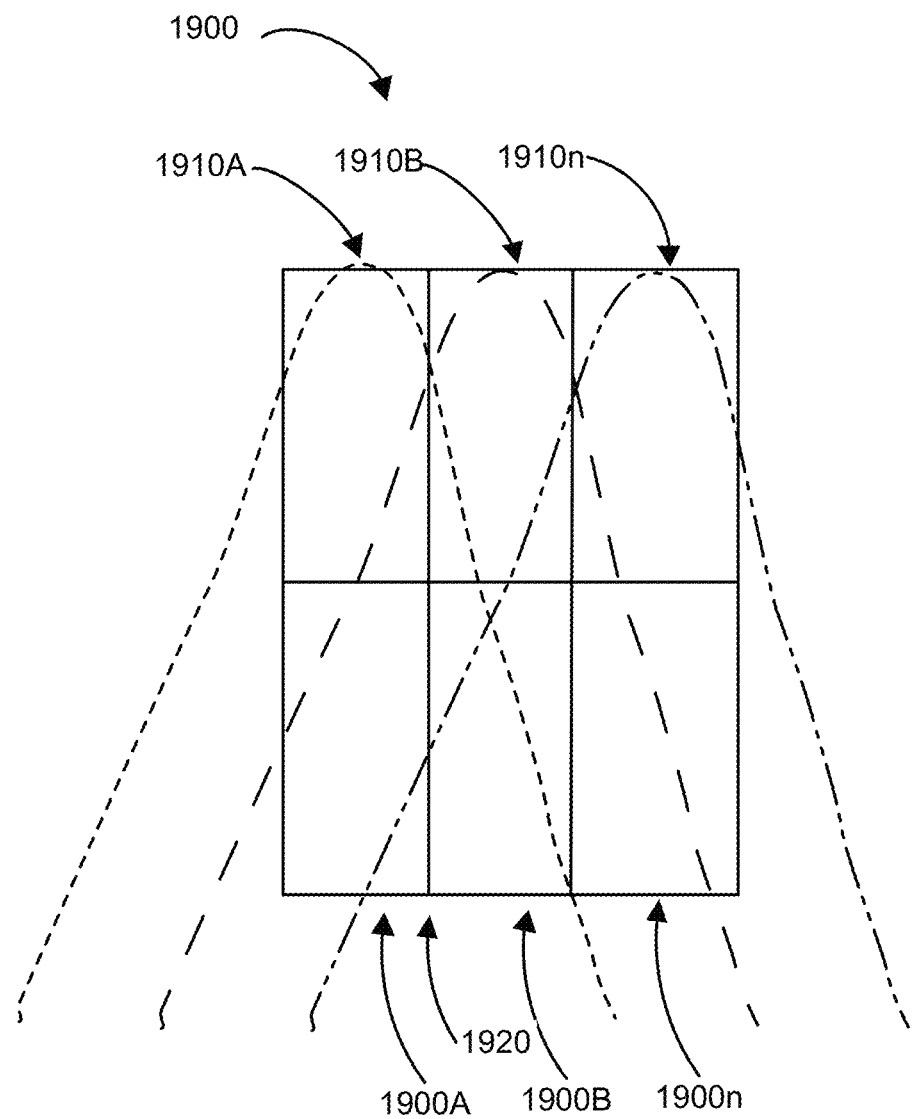
FIG. 19 is an exemplary reference matrix according to an embodiment.

FIG. 19 illustrates an exemplary reference matrix 1900 based on a treatment plan for spots 1900A, 1900B, and 1900n. The reference matrix 1900 includes a series of Gaussian distributions 1910A, 1910B, and 1900n for the "x" component of the charged particle pencil beam at spots 1900A, 1900B, and 1900n, respectively. Although not shown in FIG. 19, a similar Gaussian distribution can be mapped for spots 1900A, 1900B, and 1900n for the "y" component of the charged particle pencil beam. The Gaussian distributions 1910A, 1910B, and 1900n are centered on each spot 1900A, 1900B, and 1900n, respectively. The left-hand side 1920 of the second spot v00B intersects the Gaussian distribution 1910A of spot 1900A at σx/3, as described above. However, it is noted that the Gaussian distributions 1910A, 1910B, and 1900n distributions can be offset based on the interpolation of the x and y data from the second and third detectors, as described above (e.g., FIG. 12).

Figure 20:
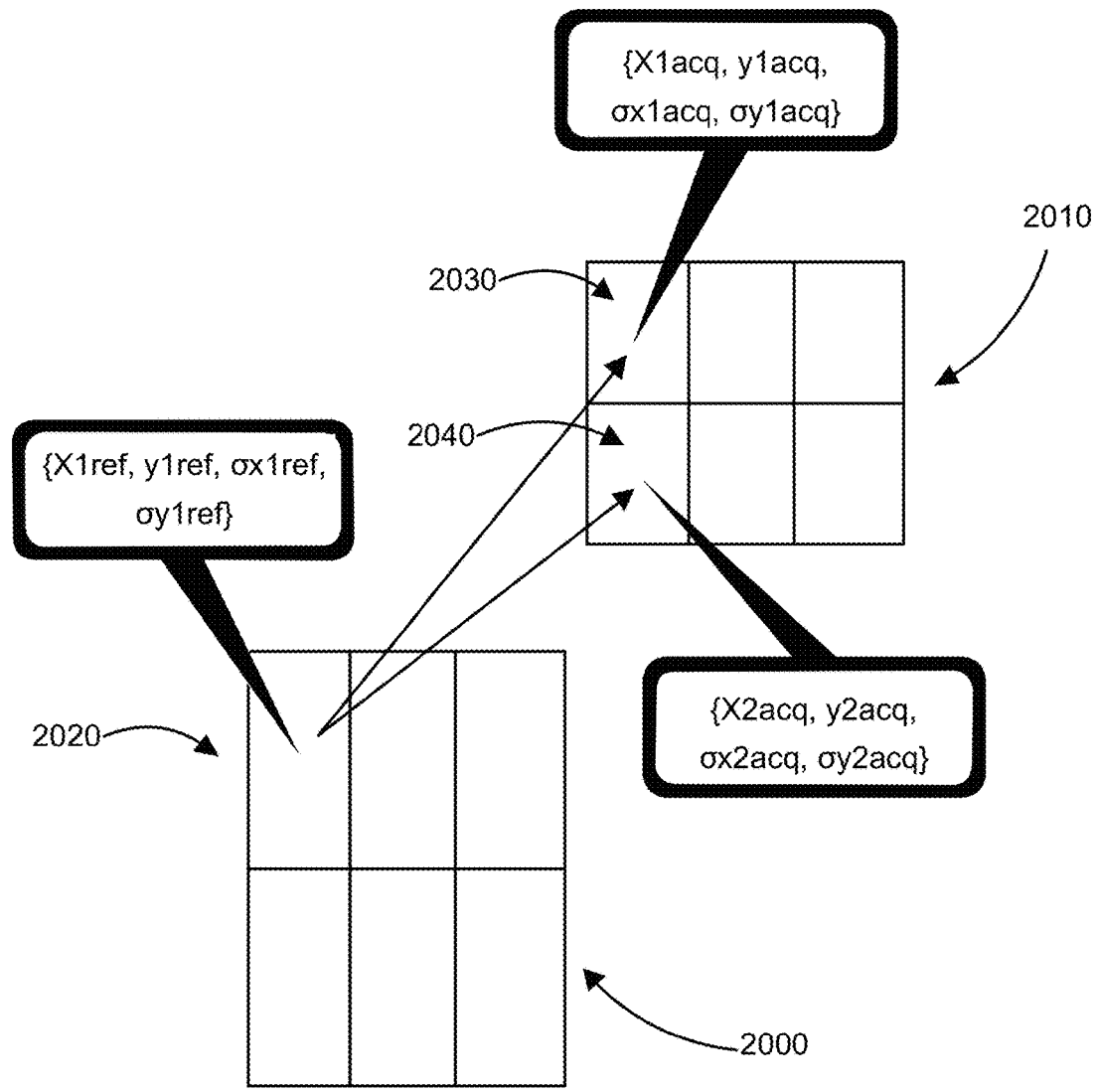
FIG. 20 is an illustration of a translation of data from a reference matrix to an acquired matrix according to an embodiment.

FIG. 20 illustrates an exemplary reference matrix 2000 and an acquired matrix 2010. As represented by the dimensions of the matrices 2000 and v10, the acquired matrix 2010 has a higher resolution than the reference matrix 2000. By interpolation and/or scaling, a first spot 2020 in reference matrix 2000 having values X1ref, y1ref, σx1ref, and σy1ref is interpolated and/or scaled to spots 2030 and 2040 in acquired matrix 2010. Spot 2030 has values of X1acq, y1acq, σx1acq, and σy1acq based on scaling and/or interpolation of the values for spot 920. Similarly, spot 940 has values of X2acq, y2acq, σx2acq, and σy2acq based on scaling and/or interpolation of the values for spot 2020. This process can be used to convert each spot in reference matrix 2000 to corresponding spots in acquired matrix 2010, as described above.

Figure 21:
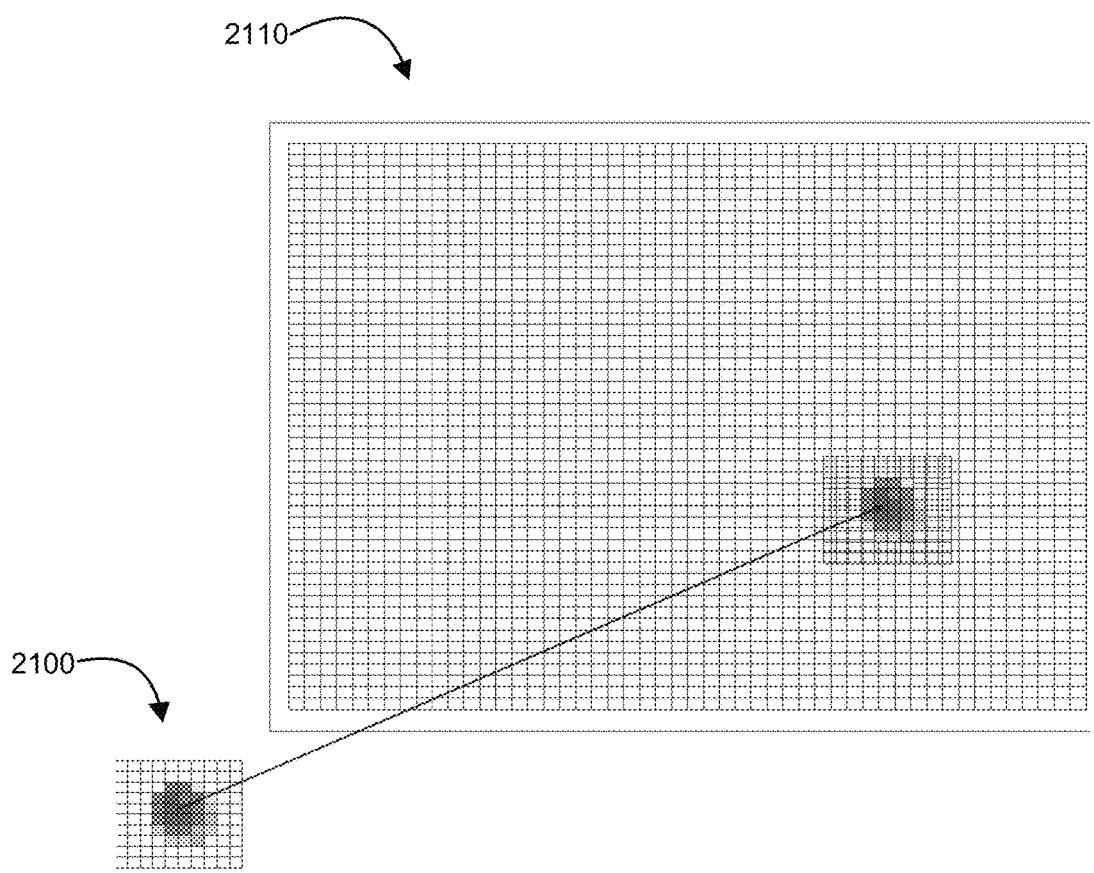
FIG. 21 is an illustration of a translation of data from a pixelated detector to an acquired matrix according to an embodiment.

FIG. 21 illustrates an exemplary mapping of data 2100 from a pixelated detector (e.g., first detector 1220) to a corresponding spot an acquired matrix 2110. As illustrated, data 2100 represents the shape and intensity distribution of a charged particle pencil beam (e.g., charged particle beam 1200). The data 2100 is scaled and summed to the acquired matrix 2110 at centroid coordinates measured by the second and third detectors 1240, 1250.

The present invention should not be considered limited to the particular embodiments described above, but rather should be understood to cover all aspects of the invention as fairly set out in the present claims. Various modifications, equivalent processes, as well as numerous structures to which the present invention may be applicable, will be readily apparent to those skilled in the art to which the present invention is directed upon review of the present disclosure. For example, the gamma distribution technique can be replaced by an auto-correlation technique as known in the art. An additional example is the application of the technique to the continuous scanning mode of delivery, in which the algorithm of FIG. 18 would assume the loop starting at step 1825 spans a single time slice. The claims are intended to cover such modifications.

What is claimed is:

1. A system for real-time dosage monitoring during therapeutic treatment of a patient, the system comprising:
   a pencil beam generator to generate a charged particle pencil beam that travels in a direction parallel to a reference axis, the charged particle beam having an intensity distribution and a shape;
   a first detector disposed in a first plane orthogonal to the reference axis and configured to dynamically generate a first output representative of the shape and the intensity distribution of the charged particle pencil beam, the first detector comprising detector elements that define pixels;
   a magnetic field generator configured to deflect the charged particle pencil beam, at an angle relative to the reference axis, to a model target location in a patient, wherein the first planar beam detector is disposed between the pencil beam generator and the magnetic field generator;
   a second detector disposed in a second plane orthogonal to the reference axis, the second detector configured to generate a second output representative of second coordinates of the charged particle pencil beam in the second plane, wherein the magnetic field generator is disposed between the first detector and the second detector;
   a third detector disposed in a third plane orthogonal to the reference axis, the third detector configured to generate a third output representative of third coordinates of the charged particle pencil beam in a third plane, wherein the second detector is disposed between the magnetic field generator and the third detector; and
   a controller comprising a processor, the controller configured to receive as inputs the first output, the second output, and the third output and to transmit an intensity control signal to the pencil beam generator and a target location control signal to the magnetic field generator.

2. The system of claim 1 wherein the second detector is a strip detector.

3. The system of claim 1 wherein the third detector is a strip detector.

4. The system of claim 1 wherein the controller is configured to compare target data for a target therapeutic treatment of a spot with actual data acquired during an actual therapeutic treatment of the spot to generate a comparison data.

5. The system of claim 4 wherein the controller is configured to automatically stop the pencil beam generator if the comparison data is greater than a tolerance.

6. The system of claim 5 further wherein the controller is in electrical communication with a display to graphically illustrate the actual data after automatically stopping the pencil beam generator.

7. The system of claim 1 wherein the first detector comprises a polymer layer disposed between a first metal layer and a second metal layer.

8. The system of claim 7 wherein the polymer layer defines a plurality of holes that extend from an upper surface of the polymer layer to a lower surface of the polymer layer.

9. The system of claim 7 wherein the polymer layer has a thickness of between about 10 and about 30 microns.

\* \* \* \* \*